United States Patent
Van Orden et al.

(10) Patent No.: US 11,373,759 B2
(45) Date of Patent: Jun. 28, 2022

(54) SYSTEMS AND METHODS FOR ESTIMATING THE RISK OF A FUTURE HYPOGLYCEMIC EVENT

(71) Applicant: Novo Nordisk A/S, Bagsvaerd (DK)

(72) Inventors: Brad Warren Van Orden, Seattle, WA (US); Tinna Bjoerk Aradottir, Copenhagen (DK); Pete Brockmeier, Copenhagen V (DK); Henrik Bengtsson, Taastrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 377 days.

(21) Appl. No.: 16/342,654

(22) PCT Filed: Oct. 24, 2017

(86) PCT No.: PCT/EP2017/077077
§ 371 (c)(1),
(2) Date: Apr. 17, 2019

(87) PCT Pub. No.: WO2018/077835
PCT Pub. Date: May 3, 2018

(65) Prior Publication Data
US 2019/0244713 A1 Aug. 8, 2019

Related U.S. Application Data

(60) Provisional application No. 62/414,988, filed on Oct. 31, 2016.

(30) Foreign Application Priority Data

Nov. 16, 2016 (EP) .................................... 16199030

(51) Int. Cl.
*A61B 5/00* (2006.01)
*G16H 50/30* (2018.01)
(Continued)

(52) U.S. Cl.
CPC ......... *G16H 50/30* (2018.01); *A61B 5/14532* (2013.01); *G16H 20/10* (2018.01);
(Continued)

(58) Field of Classification Search
CPC ........ G16H 50/20; G16H 50/30; G16H 50/70; G16H 10/60; G16H 20/10; A61B 5/7275;
(Continued)

(56) References Cited

U.S. PATENT DOCUMENTS 5,251,126 A * 10/1993 Kahn ............... G01N 35/00871
600/309
7,976,492 B2 7/2011 Brauker et al.
(Continued)

FOREIGN PATENT DOCUMENTS

JP 2015178044 A 10/2015
WO 2016019192 A1 2/2016

OTHER PUBLICATIONS

Howard Zisser et al., "Bolus Calculator: A Review of Four "Smart" Insulin Pumps," Diabetes Technology & Therapeutics. 2008, vol. 10, No. 6, pp. 441-444.
(Continued)

*Primary Examiner* — Andrey Shostak
(74) *Attorney, Agent, or Firm* — Wesley Nicolas

(57) ABSTRACT

A device (250) for estimating the risk of a future hypoglycemic event for a subject with a standing insulin regimen (206), wherein the standing insulin regimen comprises one or more types of insulin medicament dosage regimen (208), wherein each of the one or more types of insulin medicament dosage regimen (208) comprises a type of insulin medicament (210) defining one or more types of insulin medicaments. Using the evaluation of a glucose concentration, a first time derivative and an insulin on board for the subject in a current metabolic state, and the evaluation of a glucose
(Continued)

concentration, a first derivative and a historical insulin on board to estimate a hypoglycemic risk measure.

12 Claims, 9 Drawing Sheets

(51) Int. Cl.
- *G16H 50/70* (2018.01)
- *G16H 20/10* (2018.01)
- *A61B 5/145* (2006.01)
- *G16H 10/60* (2018.01)
- *G16H 50/20* (2018.01)
- *A61M 5/172* (2006.01)

(52) U.S. Cl.
CPC ............ *G16H 50/70* (2018.01); *A61B 5/4839* (2013.01); *A61B 5/7275* (2013.01); *A61B 5/746* (2013.01); *A61M 5/1723* (2013.01); *A61M 2205/52* (2013.01); *G16H 10/60* (2018.01); *G16H 50/20* (2018.01)

(58) Field of Classification Search
CPC ... A61B 5/746; A61B 5/14532; A61B 5/4839; A61M 5/1723; A61M 2205/52
See application file for complete search history.

(56) References Cited

U.S. PATENT DOCUMENTS

| | | | |
|---|---|---|---|
| 8,538,703 B2 | 9/2013 | Kovatchev et al. | |
| 8,562,587 B2 | 10/2013 | Kovatchev et al. | |
| 8,798,934 B2 | 8/2014 | Wei et al. | |
| 9,439,602 B2 | 9/2016 | Sparacino et al. | |
| 10,758,674 B2 | 9/2020 | Keenan et al. | |
| 2011/0319322 A1* | 12/2011 | Bashan | G16H 20/17 514/5.9 |
| 2012/0109687 A1 | 5/2012 | Tubb | |
| 2012/0311219 A1* | 12/2012 | Ma | G06F 19/00 710/313 |
| 2014/0039383 A1* | 2/2014 | Dobbies | A61M 5/20 604/66 |
| 2014/0107607 A1 | 4/2014 | Estes | |
| 2014/0128803 A1 | 5/2014 | Dobbies et al. | |
| 2015/0134356 A1 | 5/2015 | Atlas et al. | |
| 2015/0289821 A1* | 10/2015 | Rack-Gomer | A61B 5/168 600/365 |
| 2016/0066843 A1 | 3/2016 | Mensinger et al. | |
| 2016/0113594 A1 | 4/2016 | Koehler et al. | |
| 2016/0256629 A1* | 9/2016 | Grosman | A61B 5/4839 |
| 2017/0348483 A1* | 12/2017 | Duke | G16H 10/40 |

OTHER PUBLICATIONS http://diatribe.org/app-predicts-low-blood-sugars-three-hours-advance, accessed Apr. 10, 2017.

* cited by examiner

| Label | Number |
|---|---|
| First data set | 220 |
|   Insulin medicament record 1 | 222-1 |
|     Insulin medicament injection event 1 | 224-1 |
|     Injection event timestamp 1 | 226-1 |
|     Amount of insulin medicament 1 | 228-1 |
|     Type of insulin medicament injected 1 | 230-1 |
|   Insulin medicament record M | 222-M |
| Second data set | 235 |
|   Autonomous glucose measurement 1 | 236-1 |
|     Glucose measurement timestamp 1 | 238-1 |
|   Autonomous glucose measurement N | 236-N |
| Currrent blood glucose event | 255 |
| Current metabolic state | 256 |
| Type of metabolic state | 257 |
| Evaluation period | 260 |
| Evaluation time | 261 |
| Evaluated insulin on board | 262 |
| Evaluated glucose concentration (eval. time) | 263 |
| Evaluated rate of change of glucose (eval. time) | 264 |
| Reference historical metabolic state | 265 |
| Reference historical time period | 266 |
| Reference historical time | 267 |
| Evaluated historical glucose concentration (ref. hist. time) | 270 |
| Evaluated historical rate of change of glucose (ref. hist. time) | 271 |
| Evaluated historical insulin on board evaluated (ref. hist. time) | 272 |
| Hypoglycemic risk measure | 299 |

| | |
|---|---|
| Currrent blood glucose event | 255 |
| Current metabolic state | 256 |
| Type of metabolic state | 257 |
| Evaluation period | 260 |
| Evaluation time | 261 |
| Evaluated insulin on board | 262 |
| Evaluated glucose concentration (eval. time) | 263 |
| Evaluated rate of change of glucose (eval. time) | 264 |
| Reference historical metabolic state | 265 |
| Reference historical time period | 266 |
| Reference historical time | 267 |
| Evaluated historical glucose concentration (ref. hist. time) | 270 |
| Evaluated historical rate of change of glucose (ref. hist. time) | 271 |
| Evaluated historical insulin on board (ref. hist. time) | 272 |
| Hypoglycemic risk measure | 299 |
| Max glucose concentration | 518 |
| Time of max glucose concentration | 519 |
| Selected moving period of variance | 302 |
| Predetermined threshold | 304 |
| Severity measure | 602 |
| ⋮ | |

SYSTEMS AND METHODS FOR ESTIMATING THE RISK OF A FUTURE HYPOGLYCEMIC EVENT

CROSS-REFERENCE TO RELATED APPLICATIONS

This application is a 35 U.S.C. § 371 National Stage application of International Application PCT/EP2017/077077 (WO 2018/077835), filed Oct. 24, 2017, which claims priority to European Patent Application 16199030.4, filed Nov. 16, 2016, this application further claims priority under 35 U.S.C. § 119 of U.S. Provisional Application 62/414,988, filed Oct. 31, 2016 the contents of all above-named applications are incorporated herein by reference.

TECHNICAL FIELD

The present disclosure relates generally to systems, methods and computer programs for estimating the risk of a future hypoglycemic event for a subject with a standing insulin regimen, wherein the standing insulin regimen comprises an insulin medicament dosage regimen with one or more types of insulin medicaments in order to minimize the risk of the subject having experiencing a hypoglycemic risk.

BACKGROUND

Traditional insulin medicament delivery systems have included the use of pump systems that provide a frequent recurrent dosage of insulin medicament. Insulin pumps use only one type of insulin, namely, a short acting pump insulin, which mimics the basal and prandial insulin secretions by utilizing different pump rates during the day. Additional types of delivery systems have been developed, such as insulin pens, which can be used to self-administer insulin medicament treatment regimens in the form of less frequent insulin medicament injections. A common approach to Type 1 and Type 2 diabetes using such delivery systems is to inject a single short acting insulin medicament (bolus) dosage in a prescribed insulin regimen for the subject in response to or in anticipation of a meal event. In such approaches, the subject injects the short acting insulin medicament dosage shortly before or after one or more meals each day to lower glucose levels resulting from such meals. A long acting insulin medicament is then used to mimic the basal secretion.

Fear of hypoglycemia is one of the greatest barriers to optimal insulin treatment. Due to fear patients tend to underestimate the size of the meal bolus, which leads to non-adherent treatment and hyperglycemia with negative long-term consequences for the patient's health. Having a predictive hypoglycemia alarm constantly monitoring glucose and active insulin on board can relieve some of this fear.

Some insulin pumps have integrated hypoglycemia alarms. An app developed for insulin pumps, analyzes trends in continuous glucose data from continuous glucose monitor (CGM). The pump further analyzes carb data, insulin pump data, and an individual person's glucose history to predict future low blood sugars within three hours of taking a bolus. The hypoglycemia prediction app will rely on real-time data sent from a pump to mobile app. The information is obtained from https://diatribe.org/apppredictslowbloodsugarsthree-hoursadvance, retrieved on Oct. 12, 2016.

U.S. Pat. No. 8,562,587 B2 describes another system comprising an insulin pump and a CGM. An aspect of a described embodiment provides a method for preventing or mitigating hypoglycemia in a subject. The method may comprise obtaining metabolic measurements associated with the subject, and a continuously assessment of a risk of hypoglycemia based on the metabolic measurements. The method further comprises an evaluation of the risk of hypoglycemia to determine one of the following outcomes 1) no action is needed, 2) attenuation of insulin delivery is needed, 3) additional intervention is needed or 3) attenuation of insulin delivery and additional intervention are needed.

U.S. Pat. No. 8,538,703 B2 describes a system and a method of enhancing home blood glucose monitoring devices by introducing an intelligent data interpretation component capable of predicting both HbA1c and periods of increased risk of hypoglycemia. One aspect of the method and system for estimating long-term probability for severe hypoglycemia is based on self-monitored blood glucose (SMBG) readings from a predetermined period, and in another aspect it provides an estimate of the short-term probability.

US 2014/0128803 describes an integrated system for monitoring a glucose concentration in a host and for delivering insulin to a host. The system comprises a continuous glucose sensor, wherein the continuous glucose sensor is configured to substantially continuously measure a glucose concentration in a host, and to provide sensor data associated with the glucose concentration in the host. The system further comprises an electronics module comprising an on/off controller module configured to iteratively determine an insulin therapy instruction in response to an evaluation of a relationship of internally derived data and a glucose boundary, wherein the insulin therapy instruction comprises an instruction selected from the group consisting of on and off. The system further comprises an insulin delivery device configured to deliver insulin to the host, wherein the insulin delivery device is at least one of physically connected to a receiver and operably connected to a receiver, wherein the insulin delivery device is configured to receive the insulin therapy instruction from the controller. In some embodiments the medicament delivery device can be an infusion pump, a pen, a syringe, an inhaler, a medicament patch, and the like.

US 2012/0109687 A1 describes a medical system for providing glycemic control. The system comprises first storage means arranged to store data, first data processing means arranged to execute a first processing function for modifying data retrieved from the first storage means, second storage means arranged to store data, blood glucose measurement means arranged for measuring a blood glucose value and to provide blood glucose value data corresponding to the measured blood glucose value, second data processing means arranged to execute a second processing function for providing information for glycemic control based on the blood glucose value data and data retrieved from the second storage means, transmitting means arranged to transmit data stored in the first storage means and security data, receiving means arranged to receive the transmitted data, validating means arranged to validate the received security data and to provide validation data corresponding to the validation of the received security data, and safety means arranged to control an execution of the second processing function. The document also describes methods for selecting hypoglycemic rules. In some embodiments the medical device may comprise a pen an insulin pump or an inhale device.

WO 2016/019192 A1 describes a smart bolus injector in the form of an electronic insulin pen. First, the smart bolus injector is capable of receiving an instruction from a computing device in order to set a dose amount. Second, the smart bolus injector is capable of automatically priming the injector and delivering a bolus dose corresponding to the instruction received from the computing device. The computing device may be a separate component, such as a personal computer or smart phone, but the computing device may also be incorporated into the smart bolus injector. The smart bolus injector can include components to receive data from external devices, such as a CGM and the computing device. The document further describes an embodiment including a safety feature to shutoff the delivery system when hypoglycemia is detected. This feature responds to low blood glucose readings from the glucose sensor by stopping the bolus injector from delivering insulin.

US 2016/0066843 A1 describes a machine-executed method of continuous analyte monitoring. The method comprises receiving a first input from a module executed by an electronic device, and receiving a second input from a continuous analyte censoring device. The method comprises further processing the first and second inputs and producing an output, wherein the output that is more informative than an output produced with censor data alone. In an embodiment of the first aspect, the output is an estimate of a user's future blood glucose level after consumption of food.

U.S. Pat. No. 9,439,602 B2 describes a system for alerting a patient of hypoglycemia and hyperglycemia risk. The system includes a continuous glucose monitoring device configured to determine periodically a glucose level in the patient, thereby generating a series of glucose levels. A dynamic risk estimation module is configured to evaluate a differential change in glucose level over time (dg/dt) based on the series of glucose levels, and to generate a smoothed glucose level that is indicative of the series of glucose levels. The module is further configured to calculate dg/dt based on the series of smoothed glucose levels, and to estimate a dynamic risk based on the smoothed CGM and estimated dg/dt. A comparison circuit compares the dynamic risk to a predetermined threshold. A device monitor configured to generate a display representative of the smoothed CGM, is also configured to generate a perceptible alarm when the dynamic risk is greater than the predetermined threshold.

U.S. Pat. No. 8,798,934 B2 describes a method for estimating glucose levels using data from an integrated glucose sensor and a medicament delivery device. The method comprises receiving sensor data associated with a glucose sensor, and receiving medicament delivery data associated with a medicament delivery device. The method further comprises evaluating the medicament delivery data with the sensor data corresponding to delivery and/or release of the medicament to determine one or more individual metabolic patterns associated with medicament delivery and/or release. The method further comprises predicting a glucose value for a future time period based at least in part on the individual metabolic patterns and the sensor data, and activating an alarm when the predicted glucose value is greater than a threshold value indicative of a hyperglycemic condition or less than a threshold value indicative of a hypoglycemic condition.

US2015/0289821 disclose systems and methods that employ several factors in the determination of a glycemic urgency index, which may be based on measured blood glucose levels as well as other factors. The system may be used to drive a pump.

Despite the above background, what are still needed in the art in order to alleviate the fear of hypoglycemia, is highly reliable devices and methods for estimating the risk of a future hypoglycemic event for a subject with a standing insulin regimen, wherein the standing insulin regimen comprises an insulin medicament dosage regimen with one or more types of insulin medicaments.

SUMMARY

In the disclosure of the present invention, embodiments and aspects will be described which will address one or more of the above objects or which will address objects apparent from the below disclosure as well as from the description of exemplary embodiments.

In a first aspect is provided a device for estimating the risk of a future hypoglycemic event for a subject with a standing insulin regimen, wherein the standing insulin regimen comprises one or more types of insulin medicament dosage regimen, wherein each of the one or more types of insulin medicament dosage regimen comprises a type of insulin medicament defining one or more types of insulin medicaments;

the device comprises one or more processors and a memory, the memory storing:
one or more types of insulin medicament, and for each of the type of insulin medicament, a duration of action profile for predicting the insulin remaining in the subject as a function of time and characterized by a duration of the respective insulin medicament, wherein the type of insulin medicament can contribute to insulin on board if a corresponding injection event is having a time stamp within the duration,
a historical data set comprising historical insulin on board data for the subject as a function of time within a historical time course, historical glucose measurements of the subject and corresponding timestamps obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen,
a plurality of historical time period records obtained from the historical data set, wherein each of the historical time period records comprises an identified historical metabolic state of the subject, a historical blood glucose event, wherein the historical metabolic state can be identified by the historical blood glucose event, wherein the historical blood glucose event can be identified as a pattern in the historical glucose measurements of the historical data set, a respective type of metabolic state, and a corresponding historical time period in adherence with the standing insulin regimen, wherein the corresponding historical time period in adherence is one of the plurality of historical time periods in adherence;
the memory further storing instructions that, when executed by the one or more processors, perform a method of:
obtaining a first data set from one or more insulin injection devices used by the subject to apply the standing insulin regimen, the first data set comprising a plurality of insulin medicament records over a time course following the historical time course, each respective insulin medicament record in the plurality of medicament records comprising:
  (i) a respective insulin medicament injection event including an amount of insulin medicament injected into the subject using a respective insulin injection device in the one or more insulin injection devices, and
  (ii) a corresponding electronic injection event timestamp within the time course that is automatically generated by the respective insulin injection device upon occurrence of the respective insulin medicament injection event,
  (iii) a respective type of insulin medicament injected into the subject from one or more types of insulin medicaments;
obtaining a second data set, the second data set comprising a plurality of autonomous glucose measurements of the subject and, for each respective autonomous glucose measurement in the plurality of autonomous glucose measurements, a glucose measurement timestamp representing when the respective measurement was made, wherein the glucose measurements and the corresponding timestamps, are structured to allow a derivation of a first derivative with respect to time and thereby to obtain an evaluated glucose concentration and a rate of change of glucose as a function of time;
using the second data set to obtain a current blood glucose event associated with the subject, wherein the current blood glucose event can be identified as a pattern in the autonomous glucose measurements of the second data set, wherein the current blood glucose event identifies the beginning of an evaluation period relating to an evaluation of a current metabolic state of the subject, wherein the current metabolic state is having a respective type of metabolic state;
responsive to an identification of the current blood glucose event associated with the subject at a given time, evaluating the hypoglycemic risk at an evaluation time within the evaluation period by:
  using the second data set to obtain the type of metabolic state of the current metabolic state;
  using the first data set to obtain an evaluated insulin on board of the subject, wherein the evaluated insulin on board is calculated from a total amount of insulin medicament injected into the subject indicated by the medicament records in the first data set having injection event timestamps that are within the duration of the respective insulin medicament to the evaluation time, and therefore contribute to the insulin on board, wherein the evaluation utilizes the duration of action profile of the medicament records indicating the total amount of insulin medicament injected,
  using the second data set to obtain:
    (i) an evaluated glucose concentration at the evaluation time,
    (ii) an evaluated rate of change of glucose at the evaluation time; responsive to the evaluated rate of change being negative:
  using the plurality of historical time period records to obtain:
    (i) a reference historical metabolic state of the subject, by selecting a historical time period record, comprising a historical metabolic state having the same type of metabolic state as the current metabolic state, wherein the selected historical time period record defines a reference historical time period record,
    (ii) a reference historical time period corresponding to the reference historical time period record,
    (iii) a reference historical time, by selecting a time within the reference historical time period, wherein a progression of the reference historical metabolic state at the reference historical time is comparable to the progression of the current metabolic state at the evaluation time;
  estimating a hypoglycemic risk measure wherein the hypoglycemic risk measure is an increasing function with the number of binary risk expressions being true, wherein the binary risk expressions are:
    (i) the evaluated glucose concentration is smaller than an evaluated historical glucose concentration evaluated at the reference historical time,
    (ii) an evaluated rate of change of glucose is numerically larger than an evaluated historical rate of change of glucose evaluated at the reference historical time,
an evaluated insulin on board evaluated at the evaluation time is larger than an evaluated historical insulin on board evaluated at the reference historical time.

Hereby is provided a highly reliable device for estimating the risk of a future hypoglycemic event for subjects with standing insulin regimen applied with a pen and controlled using autonomous glucose measurements. By using historical data relating to data obtained on the subject, and in periods of adherence only, and where no hypoglycemic event has occurred, it is ensured that the data for comparison and for estimating a risk measure in a current situation is optimized.

In some embodiments, the identified blood glucose event is identified as a maximum glucose level and is related to a postprandial metabolic state. In some embodiments the step of using the second data set to identify a current blood glucose event associated with the subject further comprises using the second data set to identify a maximum glucose concentration. The step is performed responsive to receiving an indication of a meal by the user or subject, or by identifying meal ingestion in the second data set. The method further comprises identifying a time of maximum glucose concentration, corresponding to the identified maximum glucose concentration, and thereby identifying the beginning of the evaluation period (260), and wherein the current metabolic state is a postprandial state.

In some embodiments, the identified blood glucose event is related to a current fasting period, wherein the metabolic state is metabolic state characterized by fasting. In some embodiments the step of using the second data set to identify a current blood glucose event associated with the subject further comprises evaluating a moving period of variance. In response to the moving period of variance is satisfying a predefined selection criteria, this moving period of variance is selected as an indication of the beginning of the evaluation period. The selected evaluated moving period of variance defines a selected moving period of variance.

In some embodiments the device is further adapted to perform the step of identifying the beginning of the evaluation period, as the time for the beginning of the selected moving period of variance. The current metabolic state is defined as a current fasting period.

In some embodiment the device the evaluating the moving period of variance $\sigma_k^2$ across the plurality of autonomous glucose measurements, comprises using the relations:

$$\sigma_k^2 = \frac{1}{M} \sum_{i=k-M+1}^{k} (G_i - \overline{G})^2$$

wherein, $G_i$ is the $i^{th}$ autonomous glucose measurement in a portion k of the plurality of autonomous glucose measurements, M is a number of autonomous glucose measurements in the plurality of glucose measurements and represents a contiguous predetermined time span, $\overline{G}$ is the mean of the autonomous glucose measurements selected from the plurality of autonomous glucose measurements, and k is within the first time period. The predefined selection criterion is: the moving period of variance $\sigma_k^2$ is smaller than a predetermined threshold.

In some embodiments the insulin medicament dosage regimen comprises a bolus insulin medicament dosage regimen with a short acting insulin medicament, and a basal insulin medicament dosage regimen with a long acting insulin medicament. The duration of action profile for the one or more types of insulin medicament comprises: a bolus duration of action profile for the short acting insulin medicament that is characterized by a duration of the short acting insulin medicament, and a basal duration of action profile for the long acting insulin medicament that is characterized by a duration of the long acting insulin medicament. The step of using the first data set to calculate an evaluated insulin on board of the subject further comprises adding an insulin on board relating to the short acting insulin medicament with an insulin on board relating to the long acting insulin medicament. The insulin on board relating to the short acting insulin medicament is calculated from a total amount of short acting insulin medicament injected into the subject indicated by the medicament records in the first data set having injection event timestamps that are within the duration of the short acting insulin medicament to the evaluation time. The insulin on board relating to the long acting insulin medicament is calculated from a total amount of long acting insulin medicament injected into the subject indicated by the medicament records in the first data set having injection event timestamps that are within the duration of the long acting insulin medicament to the evaluation time.

In some embodiments the method further comprises communicating the hypoglycemic risk measure to a user of the device, the subject or a health care professional or a person related to the subject.

In some embodiments, the device further comprises the step of estimating a severity measure of the estimated hypoglycemic risk measure, wherein evaluating the severity $t_{hypo}$, comprises using the relations:

$$t_{hypo} = \frac{G_{low} - G}{h_G}$$

wherein, $G_{low}$ is a lower limit of the glucose level, G is the glucose level at the evaluation time, $h_G$ is the evaluated rate of change of glucose.

In some embodiment the binary risk expressions further comprises: an evaluated rate of change of insulin on board at the evaluation time (261) is negative, and numerically smaller than an evaluated historical rate of change of insulin on board evaluated at the reference historical time, and wherein the evaluated historical rate of change of insulin on board evaluated at the reference historical time is also negative.

In some embodiments the binary risk expressions further comprises: an evaluated rate of change of insulin on board at the evaluation time (261) is positive, and numerically larger than an evaluated historical rate of change of insulin on board evaluated at the reference historical time, and wherein the evaluated historical rate of change of insulin on board evaluated at the reference historical time is also positive.

In some embodiments, the binary risk expressions further comprises: an evaluated rate of change of insulin on board at the evaluation time is positive, and an evaluated historical rate of change of insulin on board evaluated at the reference historical time is negative.

In some embodiments, wherein the standing insulin regimen comprises a basal insulin medicament dosage regimen, the periods in adherence can be identified by identifying a historical blood glucose event, in an unfiltered historical blood glucose data set. In these embodiments the memory is further storing an unfiltered historical insulin medicament data set being a first unfiltered historical data set and the unfiltered historical blood glucose data set being a second unfiltered historical data set. The method comprises identifying the historical blood glucose events, as a plurality of historical fasting events using a plurality of historical autonomous glucose measurements of the subject and respective timestamps in the second unfiltered historical data set;
  applying a first characterization to each respective historical fasting event in the plurality of fasting events, wherein
    the first characterization is one of basal regimen adherent and basal regimen nonadherent,
    a respective historical fasting event is deemed basal regimen adherent when the first unfiltered historical data set includes one or more medicament records that establish, on a temporal and quantitative basis, adherence with the standing basal insulin medicament dosage regimen during the respective historical fasting event, and
    a respective historical fasting event is deemed basal regimen nonadherent when the first unfiltered historical data set fails to include one or more medicament records that establish, on a temporal and quantitative basis, adherence with the standing basal insulin medicament dosage regimen during the respective historical fasting event; and
  wherein the historical data set is based upon glucose measurements in the second unfiltered historical data set that are contemporaneous with the historical fasting events that are deemed basal regimen adherent and by excluding glucose measurements in the second unfiltered historical data set that are contemporaneous with the historical fasting events that are deemed basal regimen nonadherent.

In some embodiments where the standing insulin regimen further comprises a bolus insulin medicament dosage regimen. The method further comprises:
  identifying the historical blood glucose events as a plurality of meal events using the plurality of historical autonomous glucose measurements and the corresponding timestamps in the second historical unfiltered data set;
  applying a second characterization to each respective historical meal event in the plurality of historical meal events, wherein
    the second characterization is one of bolus regimen adherent and bolus regimen nonadherent, a respective historical meal event is deemed bolus regimen adherent when one or more historical medicament records in the first unfiltered historical data set indicates, on a temporal basis, a quantitative basis and a type of insulin medicament basis, adherence with the standing bolus insulin medicament dosage regimen during the respective meal, and a respective meal is deemed bolus regimen nonadherent when the plurality of historical medicament records fails to indicate adherence, on a temporal basis, a quantitative basis, and a type of insulin medicament basis, with the standing bolus insulin medicament dosage regimen during the respective meal; and wherein the historical data set is based upon glucose measurements in the second unfiltered historical data set that are contemporaneous with the historical meal events that are deemed basal regimen adherent and by excluding glucose measurements in the second unfiltered historical data set that are contemporaneous with the historical meal events that are deemed basal regimen nonadherent.

In a further aspect of the device, wherein a pattern in the historical glucose measurements can be a maximum glucose value, a minimum period of variance or a period of a minimum average.

In a further aspect of the device, wherein a pattern in the autonomous glucose measurements can be a maximum glucose value, a minimum period of variance or a period of a minimum average.

In a further aspect of the device, wherein the historical blood glucose event comprises a historical glucose event type, which can be identified by the pattern in the historical glucose measurements.

In a further aspect of the device, wherein the blood glucose event can be a meal event type identified as an indication of a meal event and a maximum glucose value.

In a further aspect of the device, wherein the indication of a meal event can be obtained as a direct input from the user of the device, or wherein the indication of a meal event is obtained by evaluation of autonomous glucose measurements in the second data set.

In a further aspect of the device, wherein the blood glucose event comprises a blood glucose event type, which can be identified by the pattern in the autonomous glucose measurements.

In a further aspect of the device, wherein the blood glucose event can be a fasting event type identified as an indication of a a minimum period of variance.

In a further aspect of the device, wherein using the second data set to obtain the type of metabolic state of the current metabolic state comprises identifying the current blood glucose event, and assigning the corresponding blood glucose event type of the current blood glucose event to the metabolic state.

The invention further provides a method for estimating the risk of a future hypoglycemic event for a subject with a standing insulin regimen, wherein the standing insulin regimen comprises one or more types of insulin medicament dosage regimen, wherein each of the one or more types of insulin medicament dosage regimen comprises a type of insulin medicament defining one or more types of insulin medicaments, the method comprises:

using a device;
the device comprises one or more processors and a memory, the memory storing:
for each of the type of insulin medicament, a duration of action profile predicting the insulin remaining in the subject as a function of time and characterized by a duration of the respective insulin medicament, a historical data set comprising historical insulin on board data for the subject as a function of time within a historical time course, historical glucose measurements of the subject and corresponding timestamps obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen a plurality of historical time period records, wherein each of the historical time period records comprises an identified historical metabolic state of the subject, a respective type of metabolic state, and a corresponding historical time period in adherence, wherein the corresponding historical time period in adherence is one of the plurality of historical time periods in adherence;

the memory further storing instructions that, when executed by the one or more processors, perform a method of:

obtaining a first data set from one or more insulin injection devices used by the subject to apply the standing insulin regimen, the first data set comprising a plurality of insulin medicament records over a time course, each respective insulin medicament record in the plurality of medicament records comprising:
  (i) a respective insulin medicament injection event including an amount of insulin medicament injected into the subject using a respective insulin injection device in the one or more insulin injection devices, and
  (ii) a corresponding electronic injection event timestamp within the time course that is automatically generated by the respective insulin injection device upon occurrence of the respective insulin medicament injection event,
  (iii) a respective type of insulin medicament injected into the subject from one or more types of insulin medicaments;

obtaining a second data set, the second data set comprising a plurality of autonomous glucose measurements of the subject and, for each respective autonomous glucose measurement in the plurality of autonomous glucose measurements, a glucose measurement timestamp representing when the respective measurement was made, wherein the glucose measurements and the corresponding timestamps, are structured to allow a derivation of a first derivative with respect to time and thereby to obtain an evaluated glucose concentration and a rate of change of glucose as a function of time;

using the second data set to obtain a current blood glucose event associated with the subject, wherein the current blood glucose event indicates the beginning of an evaluation period relating to an evaluation of a current metabolic state of the subject, wherein the current metabolic state is having a respective type of metabolic state;

responsive to an identification of the current blood glucose event associated with the subject at a given time, evaluating the hypoglycemic risk at an evaluation time within the evaluation period by:
using the second data set to obtain the type of metabolic state of the current metabolic state;
using the first data set to obtain an evaluated insulin on board of the subject, wherein the evaluated insulin on board is calculated from a total amount of insulin medicament injected into the subject indicated by the medicament records in the first data set having injection event timestamps that are within the duration of the respective insulin medicament to the evaluation time, wherein the evaluation utilizes the duration of action profile of the indicating medicament records,
using the second data set to obtain:
(i) an evaluated glucose concentration at the evaluation time,
(ii) an evaluated rate of change of glucose at the evaluation time; responsive to the evaluated rate of change being negative:
using the plurality of time period records to obtain:
(i) a reference historical metabolic state of the subject, by selecting a historical time period record, comprising a historical metabolic state having the same type of metabolic state as the current metabolic state, wherein the selected historical time period record defines a reference historical time period record,
(ii) a reference historical time period corresponding to the reference historical time period record,
(iii) a reference historical time, by selecting a time within the reference historical time period, wherein a progression of the reference historical metabolic state is comparable to the progression of the current metabolic state at the evaluation time;
estimating a hypoglycemic risk measure wherein the hypoglycemic risk measure is an increasing function with the number of binary risk expressions being true, wherein the binary risk expressions are:
(i) the evaluated glucose concentration is smaller than an evaluated historical glucose concentration evaluated at the reference historical time,
(ii) an evaluated rate of change of glucose is numerically larger than an evaluated historical rate of change of glucose evaluated at the reference historical time,
(iii) an evaluated insulin on board evaluated at the evaluation time is larger than an evaluated historical insulin on board evaluated at the reference historical time.

In a further aspect is provided, a computer program comprising instructions that, when executed by a computer having one or more processors and a memory, perform the method according to the present disclosure.

In a further aspect is provided, a computer-readable data carrier having stored thereon the computer program according to the present disclosure.

BRIEF DESCRIPTION OF THE DRAWINGS

FIGS. 2A and 2B collectively illustrate a device for estimating the risk of a hypoglycemic event for a subject with a standing insulin regimen in accordance with an embodiment of the present disclosure.

FIGS. 3A and 3B illustrate a device for estimating the risk of a hypoglycemic event for a subject with a standing insulin regimen in accordance with another embodiment of the present disclosure.

Like reference numerals refer to corresponding parts throughout the several views of the drawings.

DETAILED DESCRIPTION

The present disclosure relies upon the acquisition of a first and a second data set. The first data set comprising a plurality of insulin medicament records taken over a time course. Each respective insulin medicament record in the plurality of medicament records comprises (i) a respective insulin medicament injection event including an amount of insulin medicament injected into the subject using a respective insulin injection device or insulin injection device in the one or more insulin injection devices, (ii) a corresponding electronic injection event timestamp within the time course that is automatically generated by the respective insulin injection device upon occurrence of the respective insulin medicament injection event, and (iii) a respective type of insulin medicament injected into the subject from one of the one or more types of insulin medicaments. The second data set comprises a plurality of autonomous glucose measurements of the subject and, for each respective autonomous glucose measurement in the plurality of autonomous glucose measurements, a glucose measurement timestamp representing when the respective measurement was made.

Figure 1:
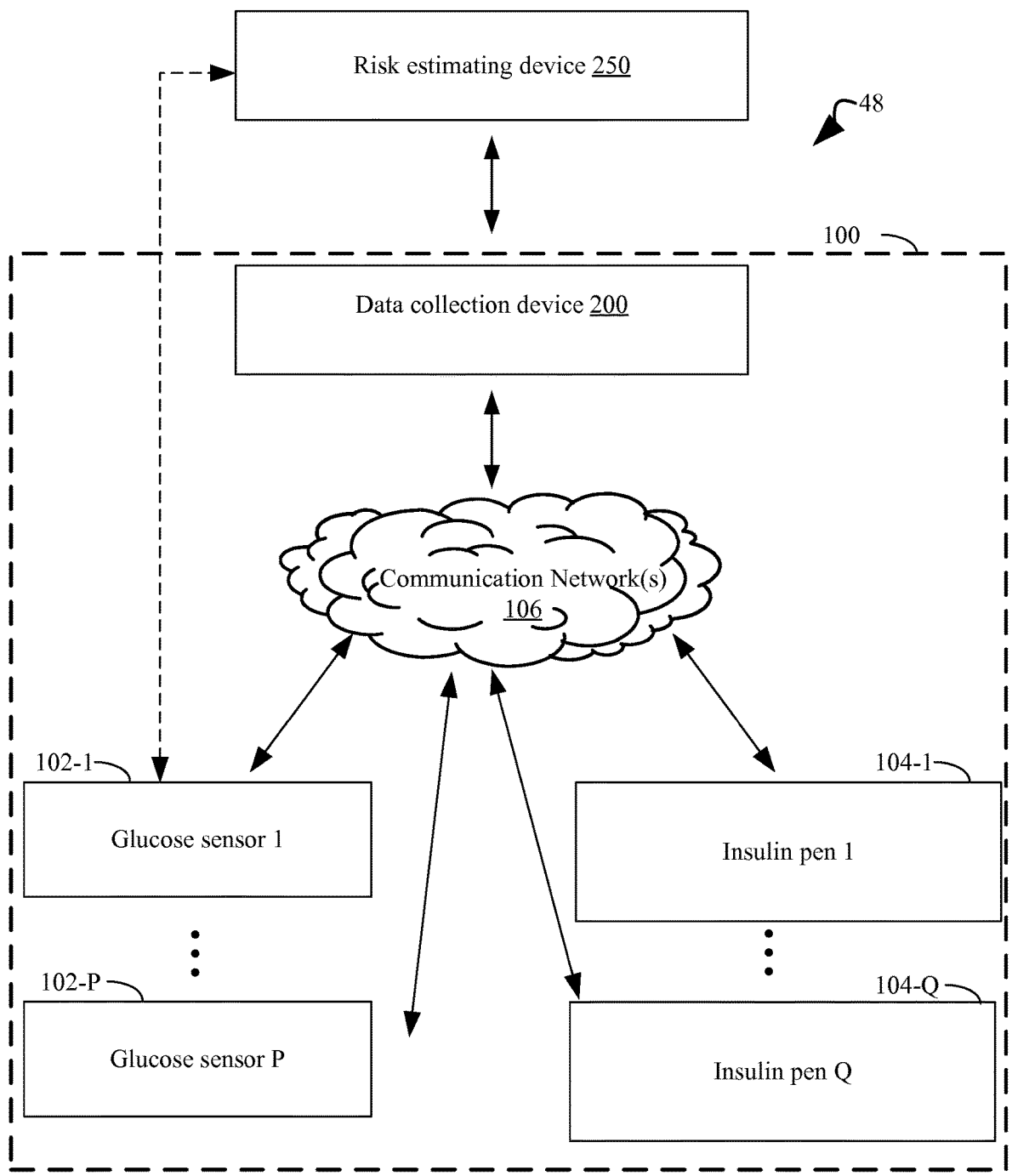
FIG. 1 illustrates an exemplary system topology that includes a hypoglycemic risk estimating device for a subject with a standing insulin regimen, a data collection device for collecting patient data, one or more glucose sensors that measure glucose data from the subject, and one or more insulin pens that are used by the subject to inject insulin medicaments in accordance with the standing insulin regimen, where the above-identified components are interconnected, optionally through a communications network, in accordance with an embodiment of the present disclosure.

FIG. 1 illustrates an example of an integrated system 100 for the acquisition of such data. The integrated system 100 includes one or more connected insulin pens 104, which is an example of an injection device. The figure illustrates further one or more glucose sensors or monitors 102, memory (not shown), and a processor (not shown) for estimating the risk of a future hypoglycemic event for a subject with a standing insulin regimen 206, wherein the standing insulin regimen comprises an insulin medicament dosage regimen 208 with one or more types of insulin medicaments 210.

With the integrated system 100, data from the one or more insulin pens 104, used to apply a standing insulin regimen to the subject, is obtained as a plurality of insulin medicament records. Each insulin medicament record comprises a time-stamped event specifying an amount of injected insulin medicament that the subject received as part of the standing insulin medicament dosage regimen. Also continuous autonomous timestamped glucose measurements of the subject are obtained. The autonomous glucose measurements are continuously filtered and stored in the memory. The plurality of insulin medicament records and the glucose measurements of the subject taken over a time course are used to estimate, in real time or close to real time, the risk of a future hypoglycemic event, in accordance with the methods of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2A:
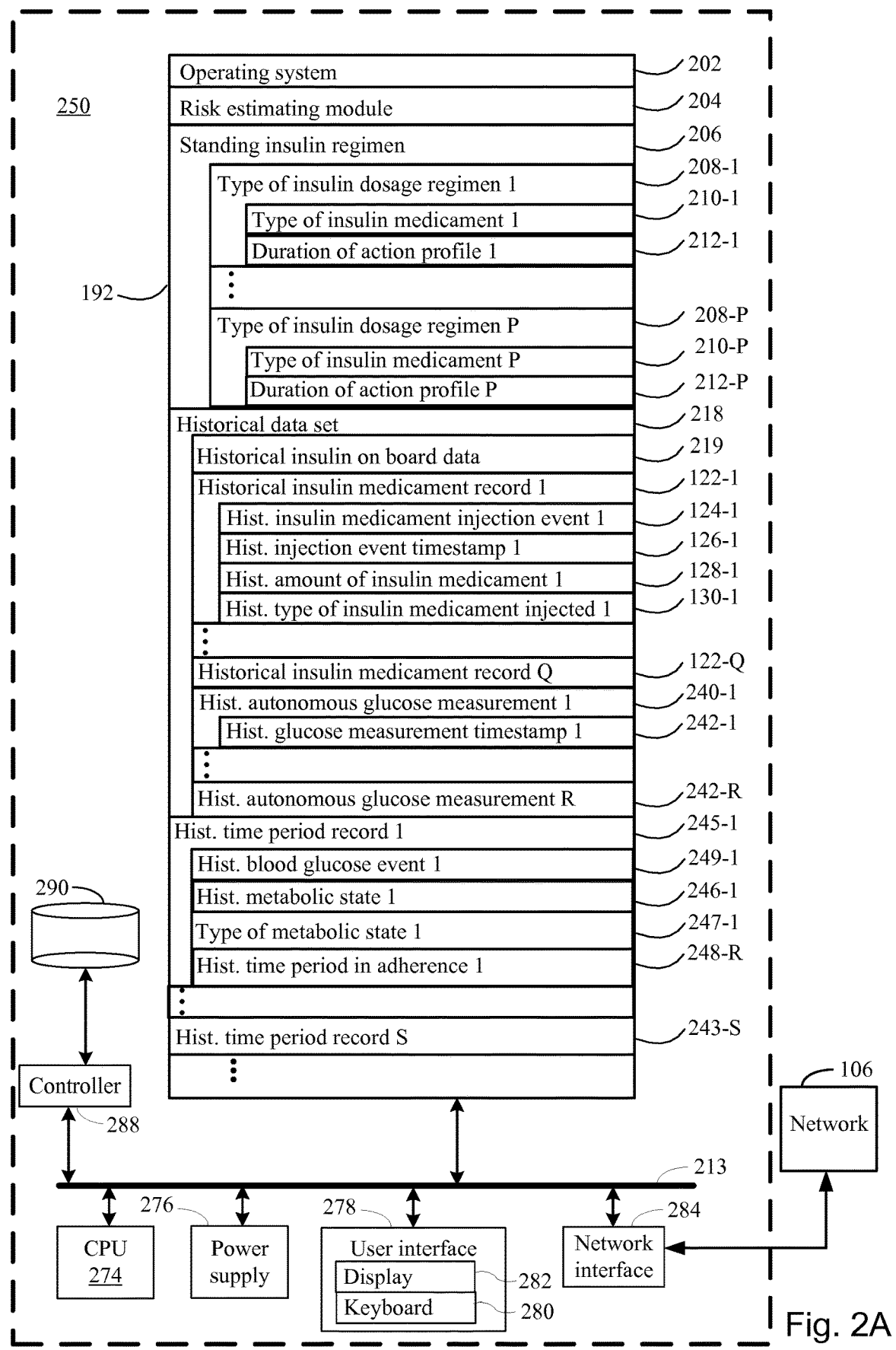

A detailed description of a system 48 for estimating the risk of a future hypoglycemic event for a subject in accordance with the present disclosure is described in conjunction with FIGS. 1 through 3. As such, FIGS. 1 through 3 collectively illustrate the topology of the system in accordance with the present disclosure. In the topology, there is a risk estimating device estimating the risk of a future hypoglycemic event for a subject (FIGS. 1, 2, and 3), a data collection device 200 for data collection, one or more insulin pens 104 for injecting insulin medicaments into the subject, and optionally one or more glucose sensors 102 associated with the subject. Throughout the present disclosure, the data collection device 200 and the risk estimating device 250 will be referenced as separate devices solely for purposes of clarity. That is, the disclosed functionality of the data collection device 200 and the disclosed functionality of the risk estimating device 250 are contained in separate devices as illustrated in FIG. 1. However, it will be appreciated that, in fact, in some embodiments, the disclosed functionality of the data collection device 200 and the disclosed functionality of the risk estimating device 250 are contained in a single device. In some embodiments, the disclosed functionality of the data collection device 200 and/or the disclosed functionality of the risk estimating device 250 are contained in a single device and this single device is an insulin pen 104.

Referring to FIG. 1, the risk estimating device 250 estimates the risk of a future hypoglycemic event for a subject. To do this, the data collection device 200, which is in electrical communication with the risk estimating device 250, receives a first 220 and a second 235 data set. The first data set 220 comprises a plurality of insulin medicament records over a time course, each record comprises (i) a respective insulin medicament injection event including an amount of insulin medicament injected into the subject using a respective insulin injection device or insulin injection device in the one or more insulin injection devices, (ii) a corresponding electronic injection event timestamp within the time course that is automatically generated by the respective insulin injection device upon occurrence of the respective insulin medicament injection event, and (iii) a respective type of insulin medicament injected into the subject from one of the one or more types of insulin medicaments. The second data set 235 comprises a plurality of autonomous glucose measurements of the subject and, for each respective autonomous glucose measurement in the plurality of autonomous glucose measurements, a glucose measurement timestamp representing when the respective measurement was made. In some embodiments, the data collection device 200 receives such data directly from the insulin pens 104 and/or glucose sensor(s) 102 and used by the subject. For instance, in some embodiments, the data collection device 200 receives this data wirelessly through radio-frequency signals. In some embodiments, such signals are in accordance with an 802.11 (WiFi), Bluetooth, or ZigBee standard. In some embodiments, the data collection device 200 receives such data directly, analyzes the data, and passes the analyzed data to the risk estimating device 250. In some embodiments, an insulin pen 104 and/or a glucose sensor 102 includes an RFID tag and communicates to the data collection device 2006 and/or the risk estimating device 250 using RFID communication. In some embodiments, the data collection device 200 also obtains or receives physiological measurements of the subject (e.g., from wearable physiological measurement devices, from measurement devices within the data collection device 200 such as a magnetometer or a thermometer, etc.).

In some embodiments, the data collection device 200 and/or the risk estimating device 250 is not proximate to the subject and/or does not have wireless capabilities or such wireless capabilities are not used for the purpose of acquiring insulin medicament injection data, autonomous glucose data, and/or physiological measurement data. In such embodiments, a communication network 106 may be used to communicate insulin medicament injection data from the one or more insulin pens 104 to the data collection device 200 and/or the risk estimating device 250, and/or autonomous glucose measurements from the glucose sensor 102 to the data collection device 200 and/or the risk estimating device 250, and/or physiological measurement data from one or more physiological measurement devices (not shown) to the data collection device 200 and/or the risk estimating device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, the data collection device 200 and/or the risk estimating device 250 is part of an insulin pen. That is, in some embodiments, the data collection device 200 and/or the risk estimating device 250 and an insulin pen 104 are a single device.

In some embodiments, there is a single glucose sensor 102 attached to the subject and the data collection device 200 and/or the risk estimating device 250 is part of the glucose sensor 102. That is, in some embodiments, the data collection device 200 and/or the risk estimating device 250 and the glucose sensor 102 are a single device.

Of course, other topologies of the system 48 are possible. For instance, rather than relying on a communications network 106, the one or more insulin pens 104 and the optional one or more glucose sensors 102 may wirelessly transmit information directly to the data collection device 200 and/or risk estimating device 250. Further, the data collection device 200 and/or the risk estimating device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the risk estimating device 250 comprises one or more computers. For purposes of illustration in FIG. 2, the risk estimating device 250 is represented as a single computer that includes all of the functionality for estimating the risk of a future hypoglycemic event for a subject with a standing insulin regimen 206. However, the disclosure is not so limited. In some embodiments, the functionality for for estimating the risk of a future hypoglycemic event for a subject with a standing insulin regimen 206 is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary risk estimating device 250 for estimating the risk of a future hypoglycemic event for a subject with a standing insulin regimen 206 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the risk estimating device 250 but that can be electronically accessed by the risk estimating device 250 over an Internet, intranet, or other form of network or electronic cable (illustrated as element 106 in FIG. 2) using network interface 284.

In some embodiments, the memory 192 of the risk estimating device 250 for estimating the risk of a future hypoglycemic event for a subject with a standing insulin regimen 206 insulin medicaments stores:

an operating system 202 that includes procedures for handling various basic system services;

an dosage risk estimating module 204;

a standing insulin regimen 206 comprising one or more types of insulin medicament dosage regimen 208, each comprising a type of insulin medicament 210 defining one or more types of insulin medicaments;

for each of the type of insulin medicament 210, a duration of action profile 212 predicting the insulin remaining in the subject as a function of time and characterized by a duration of the respective insulin medicament;

a historical adherence filtered data set 218 comprising historical insulin on board data 219 for the subject as a function of time within a historical time course, the historical insulin on board data 219, can be derived from a plurality of historical insulin medicament records 122;

historical glucose measurements 240 of the subject and corresponding timestamps 242 obtained within the historical time course, wherein the historical glucose measurements are structured to allow a derivation of a first derivative with respect to time and thereby to obtain an evaluated historical glucose concentration, and an evaluated historical rate of change of glucose as a function of time;

a plurality of historical time period records 244, wherein each of the historical time period records 245 comprises an identified historical metabolic state 246, a respective type of metabolic state 247, i.e., a metabolic state relating to a meal event or a fasting event, and a corresponding historical time period in adherence 248, wherein the corresponding historical time period in adherence (248) is one of the plurality of historical time periods in adherence;

a first data set 220 from one or more insulin injection devices used by the subject to apply the standing insulin regimen 206, the first data set 220 comprising a plurality of insulin medicament records over a time course, each respective insulin medicament record 222 in the plurality of medicament records comprises (i) a respective insulin medicament injection event 224 including an amount of insulin medicament 228 injected into the subject using a respective insulin injection device 104 in the one or more insulin injection devices, and (ii) a corresponding electronic injection event timestamp 226 within the time course that is automatically generated by the respective insulin injection device 104 upon occurrence of the respective insulin medicament injection event 224, (iii) a respective type of insulin medicament injected 230 into the subject from one or more types of insulin medicaments;

a second data set 235, the second data set comprises a plurality of autonomous glucose measurements of the subject and, for each respective autonomous glucose measurement 236 in the plurality of autonomous glucose measurements, a glucose measurement timestamp 238 representing when the respective measurement 236 was made, wherein the glucose measurements and the corresponding timestamps, are structured to allow a derivation of a first derivative with respect to time and thereby to obtain an evaluated glucose concentration and a rate of change of glucose as a function of time;

a current blood glucose event 255 associated with the subject, wherein the current blood glucose event 255 indicates the beginning of an evaluation period 260 relating to an evaluation of a current metabolic state 256 of the subject, wherein the current metabolic state 256 is having a respective type of metabolic state 257;

an evaluation time 261 within the evaluation period 260 the type of metabolic state 257 of the current metabolic state;

an evaluated insulin on board of the subject 502, wherein the evaluated insulin on board is calculated from a total amount of insulin medicament injected into the subject indicated by the medicament records 222 in the first data set 220 having injection event timestamps 226 that are within the duration of the respective insulin medicament to the evaluation time, wherein the evaluation utilizes the duration of action profile of the indicating medicament records 222;

an evaluated glucose concentration 263 at the evaluation time 261;

an evaluated rate of change of glucose 264 at the evaluation time 261;

a reference historical metabolic state (265) of the subject, selected from a historical time period record (245) from the plurality of time period records 244. The selected historical metabolic state comprises a historical metabolic state 246 having the same type of metabolic state 247 as the current metabolic state 256, wherein the selected historical time period record 245 defines a reference historical time period record;

a reference historical time period 266 corresponding to the reference historical time period record;

a reference historical time 267, selected as a time within the reference historical time period 266, wherein a progression of the reference historical metabolic state 265 is comparable to the progression of the current metabolic state 256 at the evaluation time 261;

a hypoglycemic risk measure 299 wherein the hypoglycemic risk measure 299 is evaluated as an increasing function with an increasing number of binary risk expressions being true, wherein the binary risk expressions are: (i) the evaluated glucose concentration 263 is smaller than an evaluated historical glucose concentration 270 evaluated at the reference historical time 267, (ii) an evaluated rate of change of glucose 264 is numerically larger than an evaluated historical rate of change of glucose 267 evaluated at the reference historical time 267, (iii) an evaluated insulin on board 262 evaluated at the evaluation time 261 is larger than an evaluated historical insulin on board 272 evaluated at the reference historical time 267.

In some embodiments, the hypoglycemic risk estimating module 204 is accessible within any browser (phone, tablet, laptop/desktop). In some embodiments the risk estimating module 204 runs on native device frameworks, and is available for download onto the risk estimating device 250 running an operating system 202 such as Android or iOS.

In some implementations, one or more of the above identified data elements or modules of the risk estimating device 250 for estimating the risk of a future hypoglycemic event for a subject with a standing insulin regimen 206 are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a risk estimating device 250 for estimating the risk of a future hypoglycemic event for a subject with a standing insulin regimen 206 is a smart phone (e.g., an iPHONE), laptop, tablet computer, desktop computer, or other form of electronic device (e.g., a gaming console). In some embodiments, the risk estimating device 250 is not mobile. In some embodiments, the risk estimating device 250 is mobile.

FIG. 3 provides a further description of a specific embodiment of a hypoglycemic risk estimating device 250 that can be used with the instant disclosure. The risk estimating device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the risk estimating device 250 (e.g., a touch-sensitive surface such as a touch-sensitive display system 282 of the risk estimating device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The risk estimating device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the risk estimating device 250 and/or for determining an amount of physical exertion by the subject.

It should be appreciated that the risk estimating device 250 illustrated in FIG. 3 is only one example of a multi-function device that may be used for estimating the risk of a future hypoglycemic event for a subject with a standing insulin regimen 206, and that the risk estimating device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the risk estimating device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the risk estimating device 250, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the insulin risk estimating module 204, to perform various functions for the risk estimating device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the standing insulin regimen 206, the first data set 220, and/or the second data set 238 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the risk estimating device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the risk estimating device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the risk estimating device 250, opposite the display 282 on the front of the risk estimating device 250, so that the input 280 is enabled for use as a viewfinder for still and/or video image acquisition. In some embodiments, another optical sensor 373 is located on the front of the risk estimating device 250 so that the subject's image is obtained (e.g., to verify the health or condition of the subject, to determine the physical activity level of the subject, to help diagnose a subject's condition remotely, or to acquire visual physiological measurements of the subject, etc.).

As illustrated in FIG. 3, a risk estimating device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the risk estimating device 250 is a smart phone. In other embodiments, the risk estimating device 250 is not a smart phone but rather is a tablet computer, desktop computer, emergency vehicle computer, or other form or wired or wireless networked device. In some embodiments, the risk estimating device 250 has any or all of the circuitry, hardware components, and software components found in the risk estimating device 250 depicted in FIG. 2 or 3. In the interest of brevity and clarity, only a few of the possible components of the risk estimating device 250 are shown in order to better emphasize the additional software modules that are installed on the risk estimating device 250.

In some embodiments as also shown in FIG. 2 the memory can further store a plurality of historical medicament records, wherein each of the historical medicament records 122 comprises (i) a historical insulin medicament injection event 124, (ii) a historical injection event timestamp 126, (iii) a historical amount of insulin medicament 130, and (iv) a historical type of insulin medicament injected, wherein the historical insulin on board data 219 is derivable from the plurality of historical medicament records.

Figure 3A:
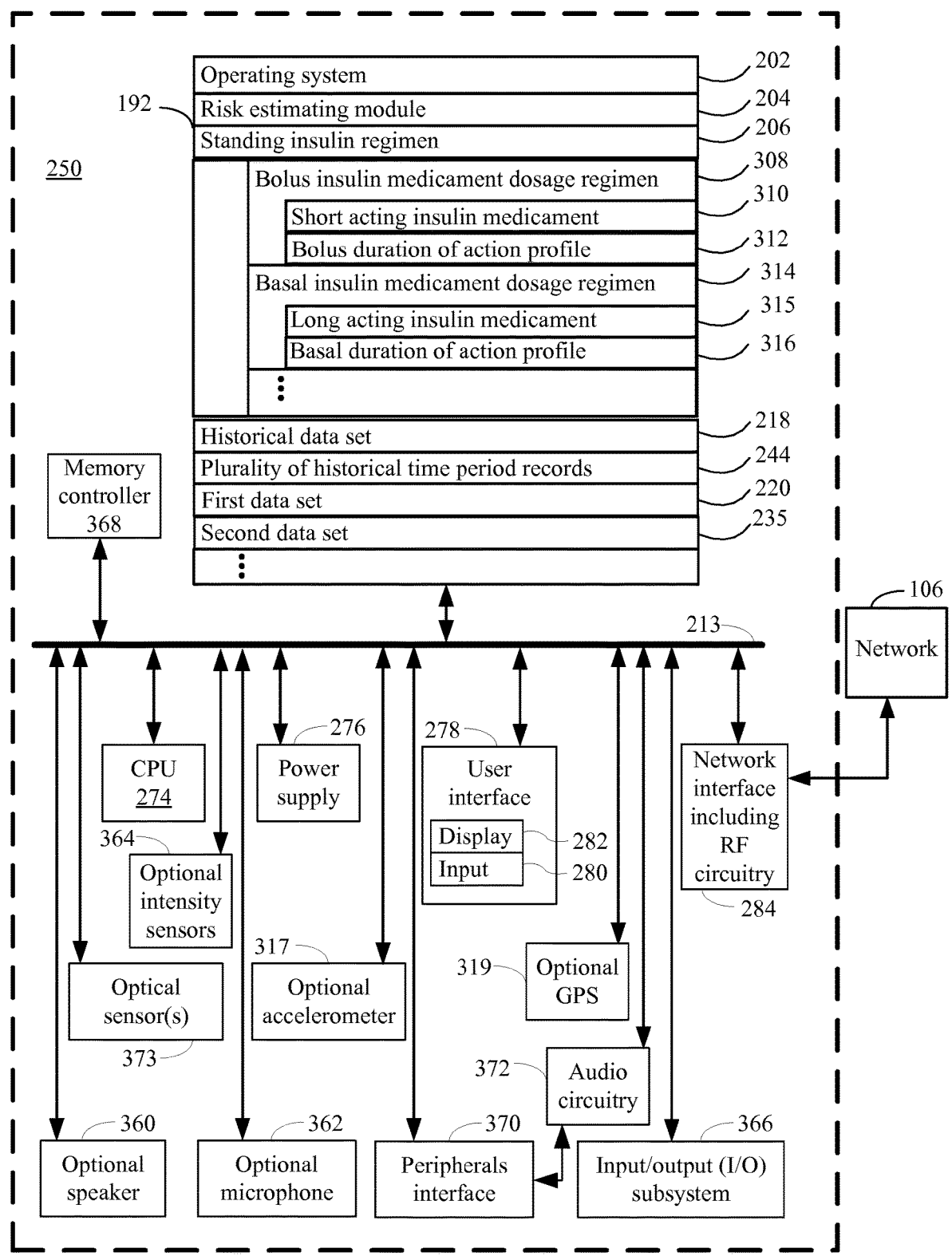

In some embodiments as also shown in FIGS. 3A and 3B the memory can further store, a maximum glucose concentration 518, a time of maximum glucose concentration 519, a selected moving period of variance (302), a predetermined threshold 304.

In some embodiments the memory can further store a bolus insulin medicament dosage regimen 308 with a short acting insulin medicament 310, and a basal insulin medicament dosage regimen 314 with a long acting insulin medicament 315. The memory can further store a bolus duration of action profile 312 for the short acting insulin medicament 310 that is characterized by a duration of the short acting insulin medicament, and a basal duration of action profile 316 for the long acting insulin medicament 315 that is characterized by a duration of the long acting insulin medicament;

In some embodiments according to the disclosure the memory can further store a severity measure 602 of the estimated hypoglycemic risk measure 299, wherein the evaluating the severity measure $t_{hypo}$, comprises using the relations:

$$t_{hypo} = \frac{G_{low} - G}{h_G}$$

wherein, $G_{low}$ is a lower limit 512 of the glucose level, G is the glucose level at the evaluation time, and $h_G$ is the evaluated rate of change of glucose 264.

While the system 48 disclosed in FIG. 1 can work standalone, in some embodiments it can also be linked with electronic medical records to exchange information in any way.

Figure 4:
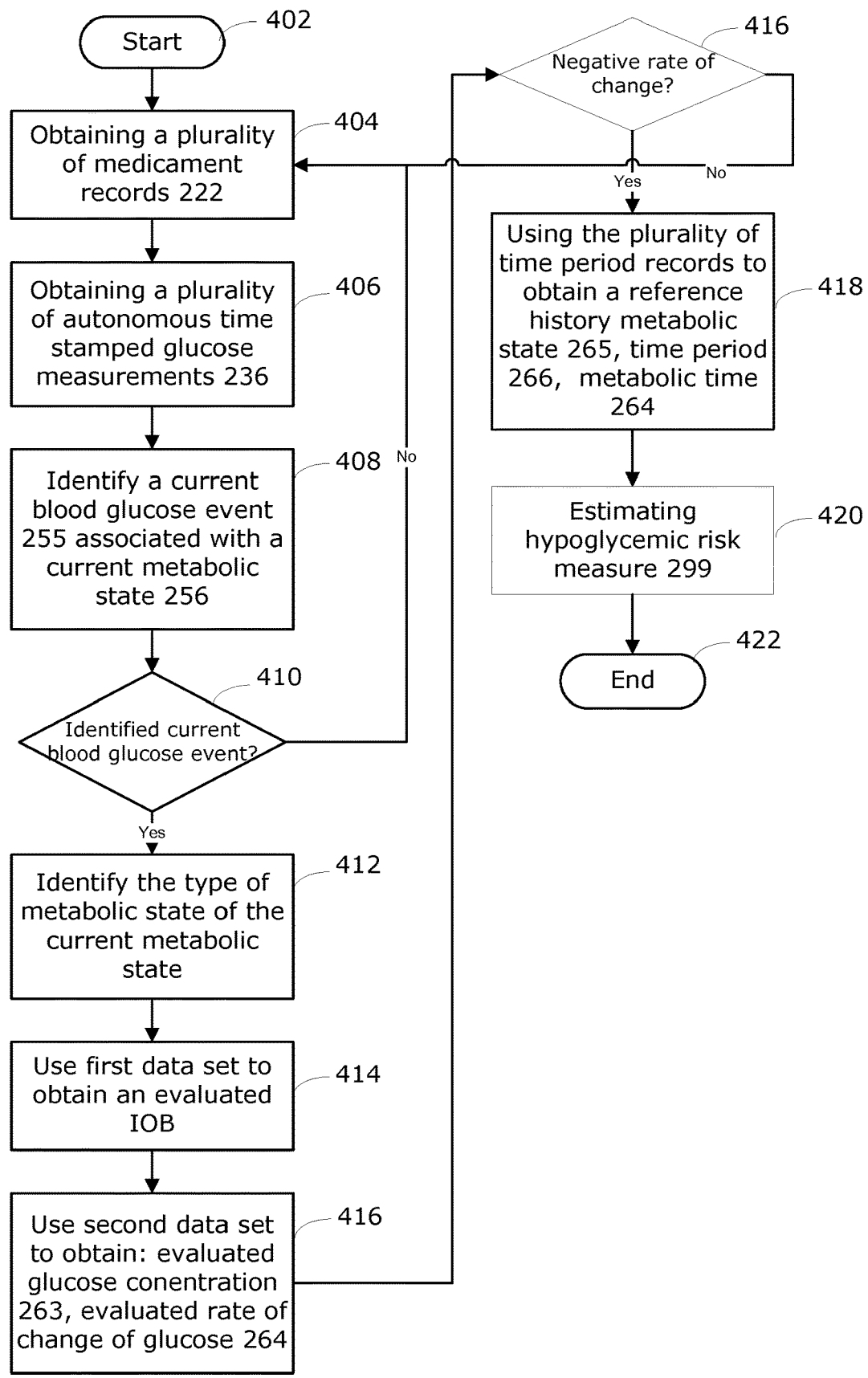
FIG. 4 provide a flow chart of processes and features of a device for estimating the risk of a hypoglycemic event for a subject with a standing insulin regimen.

Now that details of a system 48 for estimating the risk of a future hypoglycemic event for a subject with a standing insulin regimen 206 have been disclosed, details regarding a flow chart of processes and features of the system, in accordance with an embodiment of the present disclosure, are disclosed with reference to FIG. 4. In some embodiments, such processes and features of the system are carried out by the risk estimating module 204 illustrated in FIGS. 2 and 3.

FIG. 4 shows a flow diagram illustrating the method performed by the device 250 for estimating the risk of a future hypoglycemic event for a subject with a standing insulin regimen 206. The standing insulin regimen comprises one or more types of insulin medicament dosage regimen 208, wherein each of the one or more types of insulin medicament dosage regimen 208 comprises a type of insulin medicament 210 defining one or more types of insulin medicaments.

The device comprises one or more processors 274 and a memory 192/290, the memory storing: (a) for each of the type of insulin medicament 210, a duration of action profile 212 predicting the insulin remaining in the subject as a function of time and characterized by a duration of the respective insulin medicament, (b) a historical data set 218 comprising historical insulin on board data 219 for the subject as a function of time within a historical time course, historical glucose measurements 240 of the subject and corresponding timestamps 242 obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen, the historical data set 218 comprises adherence filtered data meaning it only includes data obtained in periods where the subject has been in adherence to the standing insulin regimen (c) a plurality of historical time period records 244, wherein each of the historical time period records 245 comprises an identified historical metabolic state 246 of the subject, a respective type of metabolic state 247, and a corresponding historical time period in adherence 248, wherein the corresponding historical time period in adherence 248 is one of the plurality of historical time periods in adherence.

The memory further storing instructions that, when executed by the one or more processors 274, perform a method illustrated in FIG. 4.

In block 402 the process begins. Block 404 illustrates the step of obtaining a first data set 220 from one or more insulin injection devices used by the subject to apply the standing insulin regimen 206. The first data set 220 comprises a plurality of insulin medicament records over a time course, each respective insulin medicament record 222 in the plurality of medicament records comprises: (i) a respective insulin medicament injection event 224 including an amount of insulin medicament 228 injected into the subject using a respective insulin injection device 104 in the one or more insulin injection devices, and (ii) a corresponding electronic injection event timestamp 226 within the time course that is automatically generated by the respective insulin injection device 104 upon occurrence of the respective insulin medicament injection event 224, (iii) a respective type of insulin medicament injected 230 into the subject from one or more types of insulin medicaments. Block 406 illustrates the step of obtaining a second data set 235, the second data set comprises a plurality of autonomous glucose measurements of the subject and, for each respective autonomous glucose measurement 236 in the plurality of autonomous glucose measurements, a glucose measurement timestamp 238 representing when the respective measurement 236 was made, wherein the glucose measurements and the corresponding timestamps, are structured to allow a derivation of a first derivative with respect to time and thereby to obtain an evaluated glucose concentration and a rate of change of glucose as a function of time.

Block 408 illustrates the step of using the second data set 235 to obtain a current blood glucose event 255 associated with the subject, wherein the current blood glucose event 255 indicates the beginning of an evaluation period 260 relating to an evaluation of a current metabolic state 256 of the subject, wherein the current metabolic state 256 is having a respective type of metabolic state 257.

Block 410 illustrates the conditional step which is processed at a given time. In some embodiment, if a current blood glucose event has not been found the process continues to block 404. If a current blood glucose event has been identified the process continues to block 412, i.e., responsive to an identification of the current blood glucose event 255 associated with the subject at a given time the process continues to evaluate the hypoglycemic risk at an evaluation time 261 within the evaluation period Block 412 illustrates the step of using the second data set 235 to obtain the type of metabolic state 257 of the current metabolic state 256.

Block 414 illustrates the step of using the first data set 220 to obtain an evaluated insulin on board of the subject 502, as illustrated on FIG. 5 (illustrated only for a single injection), wherein the evaluated insulin on board is calculated from a total amount of insulin medicament injected into the subject indicated by the medicament records 222 in the first data set 220 having injection event timestamps 226 that are within the duration of the respective insulin medicament to the evaluation time, wherein the evaluation utilizes the duration of action profile of the indicating medicament records 222.

Block 416 illustrates the step of using the second data set to obtain: (i) an evaluated glucose concentration 263 at the evaluation time, (ii) an evaluated rate of change of glucose 264 at the evaluation time.

Block 416 illustrates the step of receiving an indication of the evaluated rate of change of glucose 264 being negative. If the evaluated rate of change is not negative, the process can in some embodiments continue to block 404. If the rate of change 264 is negative the process continues to block 418.

Block 418 illustrates the step of using the plurality of time period records to obtain: (i) a reference historical metabolic state 265 of the subject, by selecting a historical time period record 245, comprising a historical metabolic state 246 having the same type of metabolic state 247 as the current metabolic state 256, wherein the selected historical time period record 245 defines a reference historical time period record, (ii) a reference historical time period 266 corresponding to the reference historical time period record, a reference historical time 267, by selecting a time within the reference historical time period 266, wherein a progression of the reference historical metabolic state 265 is comparable to the progression of the current metabolic state 256 at the evaluation time 261. Block 420 illustrates the step of estimating a hypoglycemic risk measure 299 wherein the hypoglycemic risk measure 299 is an increasing function with the number of binary risk expressions being true, wherein the binary risk expressions are: (i) the evaluated glucose concentration 263 is smaller than an evaluated historical glucose concentration 270 evaluated at the reference historical time 267, (ii) an evaluated rate of change of glucose 264 is numerically larger than an evaluated historical rate of change of glucose 267 evaluated at the reference historical time 267, (iii) an evaluated insulin on board 262 evaluated at the evaluation time 261 is larger than an evaluated historical insulin on board 272 evaluated at the reference historical time 267.

In some embodiments the process ends at block 422, and it can hereafter return to block 402 to start the process of estimating the risk again.

Figure 5A:
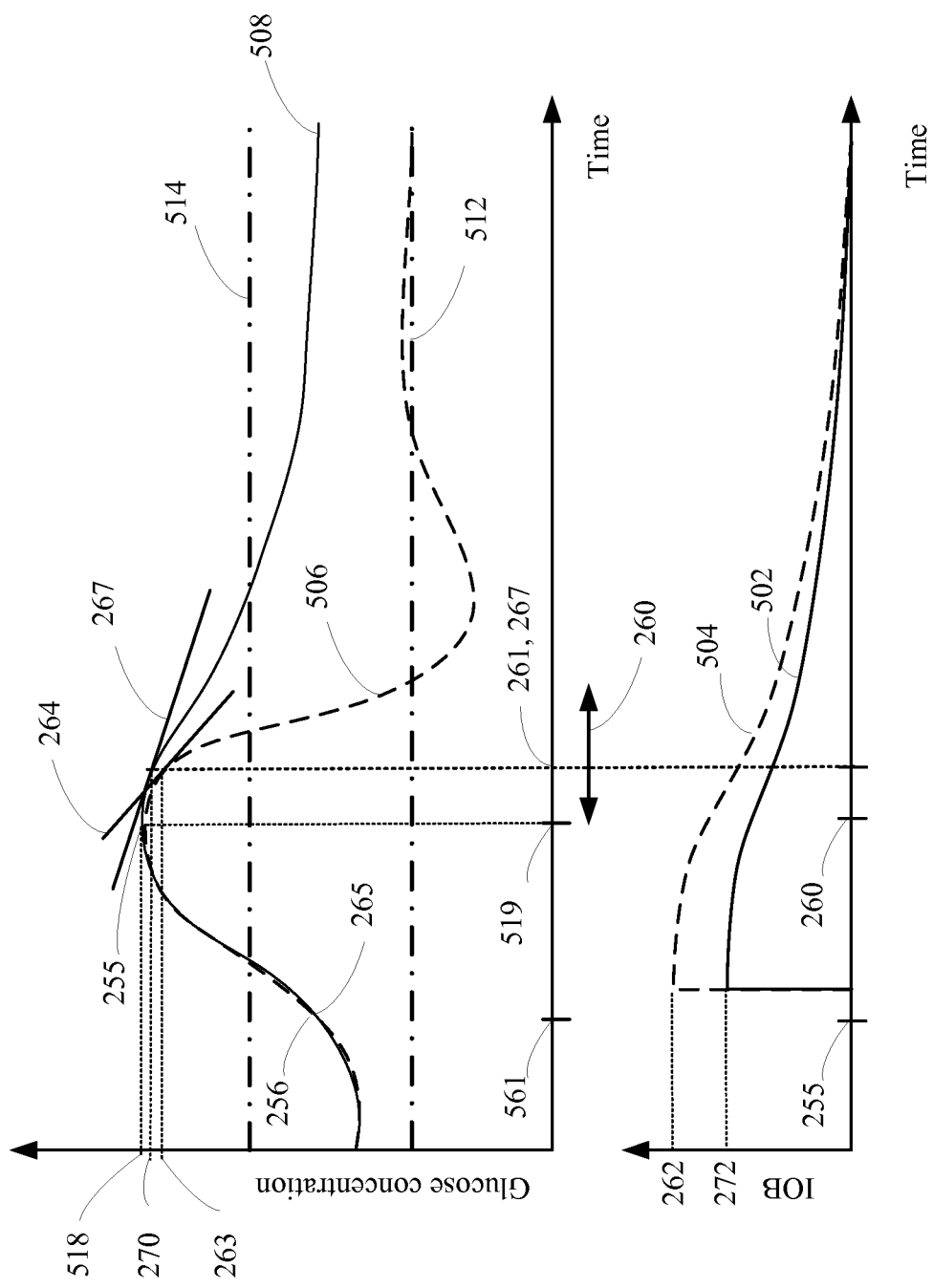
FIG. 5A illustrates the method of estimating a hypoglycemic risk in relation to a meal event accordance with an embodiment of the present disclosure.
Figure 5B:
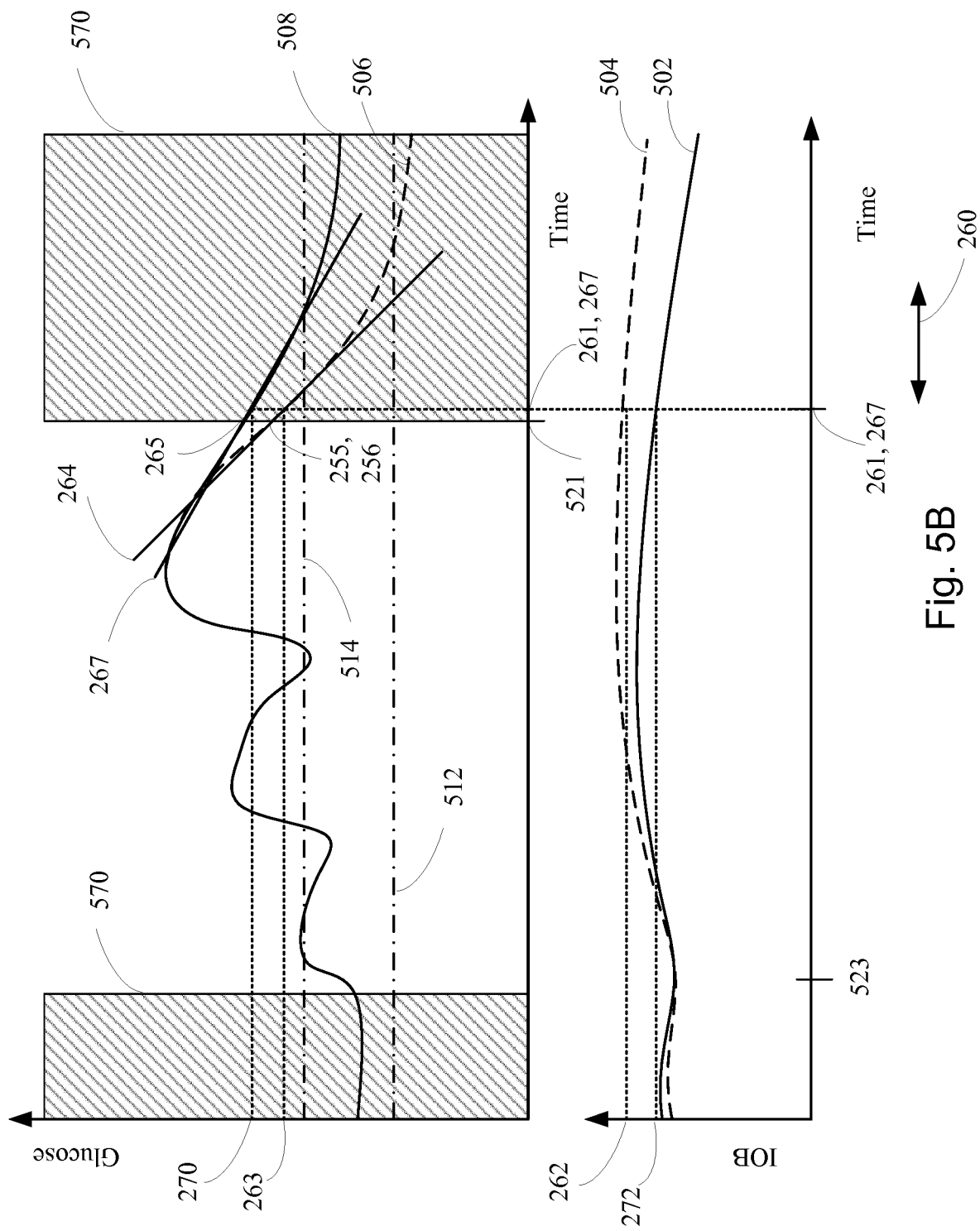
FIG. 5B illustrates the method of estimating a hypoglycemic risk in relation to a meal event accordance with another embodiment of the present disclosure.

FIGS. 5A and 5B illustrate embodiments of the disclosure wherein different blood glucose events 255 are identified.

FIG. 5A relates to an embodiment wherein using the current blood glucose event 255 associated with the subject is indicated by a maximum blood glucose level after a meal has been notified by the subject, or after a meal occurrence has been identified in the second data set using a meal detecting algorithm. The time of ingesting the meal is indicated by a meal or ingestion time 561. The meal can be notified by the subject or user of the device, wherein the subject or user actively communicate to the device that a meal has been ingested. The communication can e.g. be achieved by user operated buttons. Alternatively, a blood glucose event can be identified as a pattern, wherein the meal related blood glucose event pattern is identified as i) a maximum glucose ii) following a meal ingestion. The meal ingestion can, e.g., be identified in the second data set as a characteristic increase in the blood glucose concentration, a steep increase in the blood glucose concentration, high values of the rate of change of glucose, increase in rate of change in glucose, the maximum glucose can e.g. be identified as a zero value of the rate of change of glucose, wherein the rate of change changes from positive to negative values, when exceeding the event time of the identified zero value rate of change. The current blood glucose concentration derived from the second data set is illustrated as a dashed line curve 506, and a historical blood glucose concentration derived from the historical data 218 is illustrated as a solid line curve 508. The historical blood glucose concentration is obtained from historical glucose measurements on the subject, wherein the subject has been in adherence or compliance, and wherein the subject did not experience a hypoglycemic event in a period following the blood glucose event. That is to say, the subject has been in adherence by following the standing insulin regimen, which, as an example, could be to inject a short acting insulin before, during or after a meal. FIG. 5A also illustrates an interval of acceptable glucose concentrations, bounded by a lower limit 512 and an upper limit 514. In this interval the subject is in glycemic control. The maximum glucose after a meal indicates the blood glucose event, and time of maximum glucose 519 identifies the blood glucose event time, and it furthermore identifies the beginning of an evaluation period 260. After the maximum glucose after a meal has been identified, i.e., the blood glucose event, the current glucose concentration and the time derivative is evaluated at an evaluation time 261, which is a selected point in time within the following evaluation period 260. The current glucose concentration and the evaluation time is compared to a corresponding evaluation of the historical glucose concentrations in a historical time period at a historical reference time 267. The historical reference time 267 is having the same duration between the time of maximum glucose 519, i.e., a historical blood glucose event, and a and the reference historical time 267, as the duration between the current time of maximum glucose found, i.e., the current blood glucose event, identified in the second data set (or communicated by the user) and the evaluation time 261. A metabolic state is associated with the blood glucose event, and in the case of a meal related blood glucose event, the associated metabolic state is a postprandial state as it occurs after the meal. The blood glucose event can be used as a reference to measure the progression of the metabolic state, by measuring time from the occurrence of the blood glucose event to a given time or evaluation time within the evaluation period. In this way the progression of the reference historical metabolic state 265, time from the reference blood glucose event to the reference historical evaluation time, is comparable to the progression of the current metabolic state 256, time from the current blood glucose event to the evaluation time. However, instead of choosing the occurrence of the blood glucose event as the reference time for measuring progression other time events as the meal ingestion could be used. If, for the comparison of the current and historical metabolic state at the same progression, the current blood glucose concentration is smaller than the historical blood glucose concentration, the hypoglycemic risk is larger as the current concentration is closer to the lower boundary 512. If further more the first time derivative of the blood glucose concentration is negative and numerically larger than a negative first derivative of the historical blood glucose concentration, the hypoglycemic risk is also larger in the current situation, as the situation or metabolic state develops towards a risk with higher speed. If further more the current insulin on board, calculated from all injections in the time period of the relevant previous duration of action, the hypoglycemic risk is even greater. FIG. 5A also shows curves for the historical insulin on board 502, and the current insulin on board obtained from the first data set. In order to improve the estimates higher derivatives (second derivative, third derivative etc.) of the current glucose concentrations and first and higher derivatives (second derivative, third derivative etc.) of the insulin on board can be used to improve the estimate of the hypoglycemic risk.

FIG. 5B relates to an embodiment wherein using the current blood glucose event 255 associated with the subject, is indicated by a minimum variance within the blood glucose concentrations, wherein the minimum variance is obtained from the second data set. The step of using the second data set to identify the minimum variance can be obtained by evaluating a moving period of variance 302, in response to the moving period of variance is a minimum, selecting the evaluated moving period of variance as an indication of the beginning of the evaluation period 260. Alternatively the mean, the median, the beginning or the end of the minimum period of variance is used to indicate the beginning of the evaluation period 260. In this way the minimum variance indicates the blood glucose event, which is a fasting event, and the the associated metabolic state following the minimum variance is a fasting state. The current blood glucose concentration derived from the second data set is illustrated as a dashed line curve 506, and a historical blood glucose concentration derived from the historical data 218 is illustrated as a solid line curve 508. The historical blood glucose concentration is obtained from historical glucose measurements of the subject, wherein the subject has been in adherence or compliance with the standing insulin regimen, and wherein the subject did not experience a hypoglycemic event in a period following the blood glucose event. That is to say, the subject has been in adherence by following the standing insulin regimen, which, as an example, could be to inject a long acting insulin on a recurring basis, e.g., twice daily, once daily or once weekly. The blood glucose level within a fasting period can be indicative of whether an appropriate amount of long acting insulin has been administrated. FIG. 5B also illustrates an interval of acceptable glucose concentrations, bounded by a lower limit 512 and an upper limit 514. In this interval the subject is in glycemic control. After the blood glucose event 255, which in this case is pattern identified by the minimum variance of glucose concentration within a period, has been identified, the time of occurrence of the event indicates the beginning of an evaluation period 260. The current glucose concentration and the time derivative, rate of change, is evaluated at an evaluation time 261 within the following evaluation period 260. The evaluation of the glucose concentration at the evaluation time 261 can be compared to a corresponding evaluation of the historical glucose concentrations in a historical time period at a historical reference time 267 having the same progression in metabolic state.

The progression of the historical metabolic state can be evaluated as the duration between a time 521 of minimum variance in the historical glucose concentration and the reference historical time 267. Similarly the progression in the current metabolic state can be evaluated as the duration between the time of minimum variance (e.g., the time can be beginning of, end of, median of or mean of period having a minimum variance) in the current glucose concentrations obtained from the second data set, and the evaluation time 261. In this way the progression of the reference historical metabolic state 265 is comparable to the progression of the current metabolic state 256. If the current blood glucose concentration is smaller than the historical blood glucose concentration, the hypoglycemic risk is larger as the current concentration is closer to the lower boundary 512. If further more the first time derivative, rate of change, of the blood glucose concentration is negative and numerically larger than a negative first derivative of the historical blood glucose concentration, the hypoglycemic risk is also larger in the current situation, as the situation or metabolic state develops with higher speed. If further more the current insulin on board, calculated from all injections in the time period of the relevant previous duration of action, the hypoglycemic risk is even greater. FIG. 5B also shows curves for the historical insulin on board 502, and the current insulin on board obtained from the first data set. A time of injection 523 with a long acting insulin is also indicated. In order to improve the estimates higher derivatives of the current glucose concentrations and first and higher derivatives of the insulin on board can be used to improve the estimate of the hypoglycemic risk. Fasting periods 570 are also indicated.

In an alternative embodiment, the blood glucose event can be identified as a moving period of glucose measurements, and the time indicating the beginning of the evaluation period 260 can be the beginning of the period, end of the period, median of the period or mean of the period identified os the period having a minimum average of glucose measurements.

The historical data set 218 comprising (i) historical insulin on board data 219 for the subject as a function of time within a historical time course, (ii) historical glucose measurements 240 of the subject and corresponding timestamps 242 obtained within the historical time course, also comprises (iii) a plurality of historical time periods in adherence, and the historical time periods in adherence indicates periods wherein the subject has been in adherence with the standing insulin regimen. The historical data set 218 can be used to obtain a structured plurality of historical time period records, wherein each of the historical time period record 245 comprises an identified historical metabolic state 246 and a historical blood glucose event. The historical metabolic state can be identified by the historical blood glucose event, wherein the historical blood glucose event can be identified as a pattern in the historical glucose measurements of the historical data set 218. Each of the historical time period records further comprises a respective type of metabolic state 247, and a corresponding historical time period in adherence 248, which is a period in adherence with the standing insulin regimen.

The plurality of historical time periods in adherence, can be identified by: (i) identifying a plurality of historical blood glucose events using a plurality of unfiltered historical glucose measurements of the subject and the respective timestamps to identify a plurality of blood glucose patterns in the unfiltered historical glucose measurements, (ii) applying a first characterization to each respective historical blood glucose event in the plurality of historical blood glucose events, wherein the first characterization is one of regimen adherent and regimen nonadherent, a respective historical blood glucose event is deemed regimen adherent when a set of historical insulin injection events and corresponding time stamps establish, on a temporal and quantitative basis, adherence with the standing insulin medicament dosage regimen during the respective historical blood glucose event, and a respective historical blood glucose event is deemed basal regimen nonadherent when the set of historical insulin injection events and corresponding time stamps fails to include one or more medicament records that establish, on a temporal and quantitative basis, adherence with the standing basal insulin medicament dosage regimen during the respective historical blood glucose event.

Figure 6:
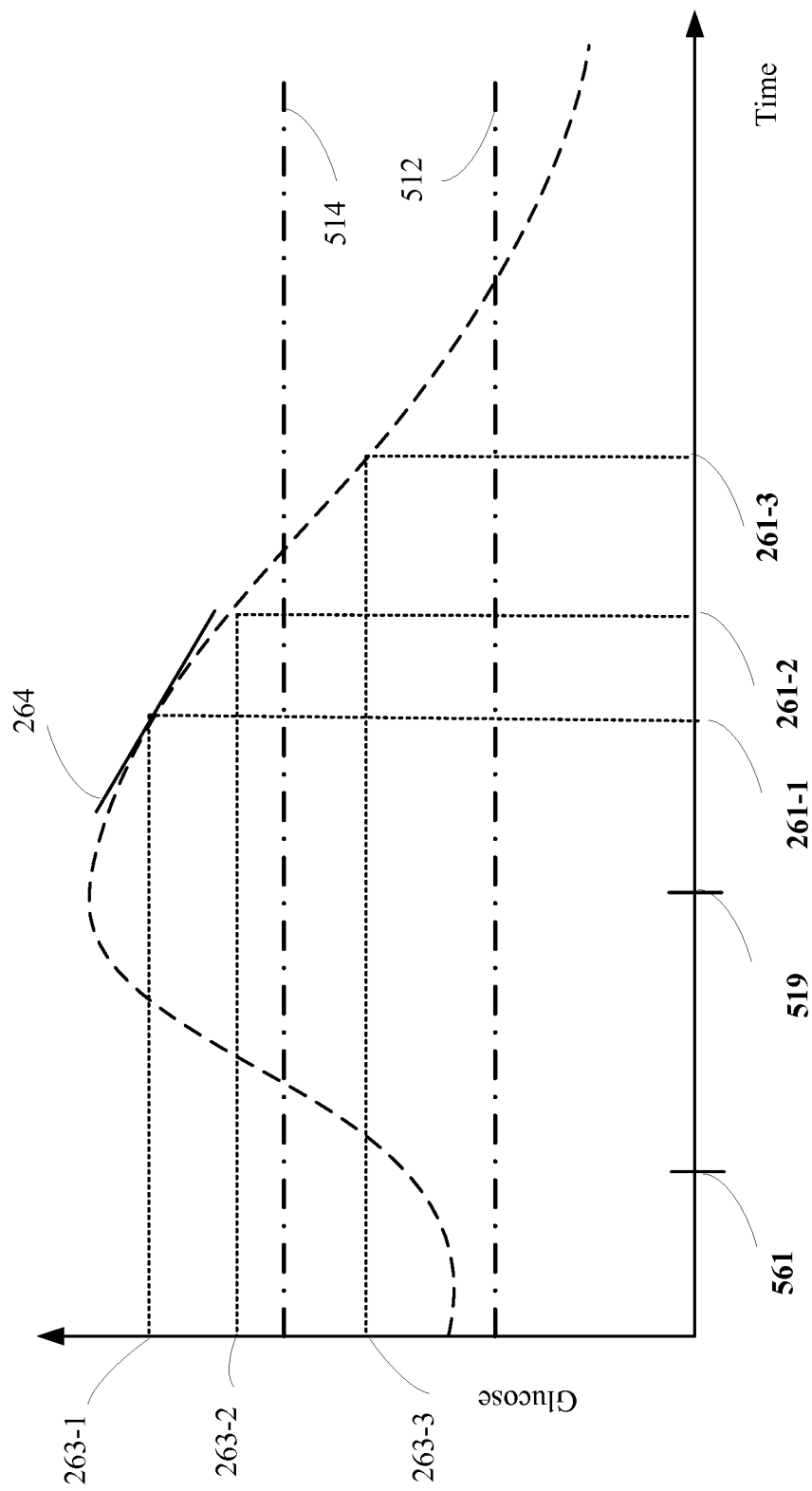
FIG. 6 illustrates the method of estimating the severity of a hypoglycemic risk at the time of evaluation.

FIG. 6 illustrates an embodiment according to the current disclosure. A hypo-alarm could have different severities, depending on when the hypo is expected. FIG. 6 illustrates the glucose concentrations in a period around a meal. The time of ingestion or meal time 561 and the time of maximum glucose concentration 519 after the meal are illustrated. Lower 512 and upper 514 glucose boundaries are also illustrated. Furthermore, different evaluation time 261-1, 261-2, 261-3 and the corresponding evaluation of blood glucose concentration 263-1, 263-2, 263-3 are indicated. The time derivative 264-1 at the evaluation time 261-1 is also indicated. At the evaluation time 261-3 the hypoglycemic risk is more severe as the hypoglycemic risk evaluated at the evaluation time 261-1, as there is a shorter time to the hypoglycemic event. evaluating the severity $t_{hypo}$, comprises using the relations:

$$t_{hypo} = \frac{G_{low} - G}{h_G}$$

wherein, $G_{low}$ is a lower limit 512 of the glucose level, G is the glucose level at the evaluation time, $h_G$ is the evaluated rate of change of glucose 264.

LIST OF EMBODIMENTS

1. A device 250 for estimating the risk of a future hypoglycemic event for a subject with a standing insulin regimen 206, wherein the standing insulin regimen comprises one or more types of insulin medicament dosage regimen 208, wherein each of the one or more types of insulin medicament dosage regimen 208 comprises a type of insulin medicament 210 defining one or more types of insulin medicaments;

the device comprises one or more processors 274 and a memory 192/290, the memory storing:
for each of the type of insulin medicament 210, a duration of action profile 212 predicting the insulin remaining in the subject as a function of time and characterized by a duration of the respective insulin medicament,
a historical data set 218 comprising historical insulin on board data 219 for the subject as a function of time within a historical time course, historical glucose measurements 240 of the subject and corresponding timestamps 242 obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen
a plurality of historical time period records 244, wherein each of the historical time period records 245 comprises an identified historical metabolic state 246 of the subject, a respective type of metabolic state 247, and a corresponding historical time period in adherence 248, wherein the corresponding historical time period in adherence 248 is one of the plurality of historical time periods in adherence;
the memory further storing instructions that, when executed by the one or more processors 274, perform a method of:
obtaining a first data set 220 from one or more insulin injection devices used by the subject to apply the standing insulin regimen 206, the first data set 220 comprising a plurality of insulin medicament records over a time course, each respective insulin medicament record 222 in the plurality of medicament records comprising:
(i) a respective insulin medicament injection event 224 including an amount of insulin medicament 228 injected into the subject using a respective insulin injection device 104 in the one or more insulin injection devices, and
(ii) a corresponding electronic injection event timestamp 226 within the time course that is automatically generated by the respective insulin injection device 104 upon occurrence of the respective insulin medicament injection event 224,
(iii) a respective type of insulin medicament injected 230 into the subject from one or more types of insulin medicaments;
obtaining a second data set 235, the second data set comprising a plurality of autonomous glucose measurements of the subject and, for each respective autonomous glucose measurement 236 in the plurality of autonomous glucose measurements, a glucose measurement timestamp 238 representing when the respective measurement 236 was made, wherein the glucose measurements and the corresponding timestamps, are structured to allow a derivation of a first derivative with respect to time and thereby to obtain an evaluated glucose concentration and a rate of change of glucose as a function of time;
using the second data set 235 to obtain a current blood glucose event 255 associated with the subject, wherein the current blood glucose event 255 indicates the beginning of an evaluation period 260 relating to an evaluation of a current metabolic state 256 of the subject, wherein the current metabolic state 256 is having a respective type of metabolic state 257;
responsive to an identification of the current blood glucose event 255 associated with the subject at a given time, evaluating the hypoglycemic risk at an evaluation time 261 within the evaluation period by:
using the second data set 235 to obtain the type of metabolic state 257 of the current metabolic state 256;
using the first data set 220 to obtain an evaluated insulin on board of the subject 502, wherein the evaluated insulin on board is calculated from a total amount of insulin medicament injected into the subject indicated by the medicament records 222 in the first data set 220 having injection event timestamps 226 that are within the duration of the respective insulin medicament to the evaluation time, wherein the evaluation utilizes the duration of action profile of the indicating medicament records 222, using the second data set to obtain:
(i) an evaluated glucose concentration 263 at the evaluation time,
(ii) an evaluated rate of change of glucose 264 at the evaluation time;

responsive to the evaluated rate of change 264 being negative:

using the plurality of historical time period records to obtain:
(i) a reference historical metabolic state 265 of the subject, by selecting a historical time period record 245, comprising a historical metabolic state 246 having the same type of metabolic state 247 as the current metabolic state 256, wherein the selected historical time period record 245 defines a reference historical time period record,
(ii) a reference historical time period 266 corresponding to the reference historical time period record,
(iii) a reference historical time 267, by selecting a time within the reference historical time period 266, wherein a progression of the reference historical metabolic state 265 is comparable to the progression of the current metabolic state 256 at the evaluation time 261;

estimating a hypoglycemic risk measure 299 wherein the hypoglycemic risk measure (299) is an increasing function with the number of binary risk expressions being true, wherein the binary risk expressions are:
(i) the evaluated glucose concentration 263 is smaller than an evaluated historical glucose concentration 270 evaluated at the reference historical time 267,
(ii) an evaluated rate of change of glucose 264 is numerically larger than an evaluated historical rate of change of glucose 267 evaluated at the reference historical time 267,
(iii) an evaluated insulin on board 262 evaluated at the evaluation time 261 is larger than an evaluated historical insulin on board 272 evaluated at the reference historical time 267.

2. The device according to embodiment 1, wherein the step of using the second data set 235 to identify a current blood glucose event 255 associated with the subject comprises:

responsive to receiving an indication of a meal, using the second data set to identify a maximum glucose concentration 518,
identifying a time of maximum glucose concentration 519, corresponding to the identified maximum glucose concentration 518, and thereby identifying the beginning of the evaluation period 260, and wherein the current metabolic state is a postprandial state.

3. The device according to embodiment 1, wherein the step of using the second data set 235 to identify a current blood glucose event 255 associated with the subject comprises:

evaluating a moving period of variance 302,
in response to the moving period of variance satisfying a predefined selection criteria, selecting the evaluated moving period of variance as an indication of the beginning of the evaluation period 260, wherein the selected evaluated moving period of variance defines a selected moving period of variance 302.

4. The device according to embodiment 3, further comprising the step of:

identifying the beginning of the evaluation period 260, as the time for the beginning of the selected moving period of variance 302, and wherein the current metabolic state (265) is a current fasting period.

5. The device according to any of the embodiments 3 or 4, wherein evaluating the moving period of variance $\sigma_k^2$, across the plurality of autonomous glucose measurements 236, comprises using the relations:

$$\sigma_k^2 = \frac{1}{M} \sum_{i=k-M+1}^{k} (G_i - \overline{G})^2$$

wherein,
$G_i$ is the $i^{th}$ autonomous glucose measurement in a portion k of the plurality of autonomous glucose measurements,
M is a number of autonomous glucose measurements in the plurality of glucose measurements and represents a contiguous predetermined time span,
$\overline{G}$ is the mean of the autonomous glucose measurements selected from the plurality of autonomous glucose measurements, and
k is within the first time period;
wherein the predefined selection criteria is: the moving period of variance $\sigma_k^2$ is smaller than a predetermined threshold 304.

6. The device according to any of the previous embodiments, wherein the insulin medicament dosage regimen comprises a bolus insulin medicament dosage regimen 308 with a short acting insulin medicament 310, and a basal insulin medicament dosage regimen 314 with a long acting insulin medicament 315; wherein the duration of action profile for the one or more types of insulin medicament comprises:
a bolus duration of action profile 312 for the short acting insulin medicament 310 that is characterized by a duration of the short acting insulin medicament, and
a basal duration of action profile 316 for the long acting insulin medicament 315 that is characterized by a duration of the long acting insulin medicament; wherein using the first data set 220 to calculate an evaluated insulin on board of the subject comprises adding an insulin on board relating to the short acting insulin medicament 310 with an insulin on board relating to the long acting insulin medicament 315, wherein
the insulin on board relating to the short acting insulin medicament is calculated from a total amount of short acting insulin medicament injected into the subject indicated by the medicament records in the first data set having injection event timestamps that are within the duration of the short acting insulin medicament to the evaluation time 260, and wherein
the insulin on board relating to the long acting insulin medicament is calculated from a total amount of long acting insulin medicament injected into the subject indicated by the medicament records in the first data set having injection event timestamps that are within the duration of the long acting insulin medicament to the evaluation time 260.

7. The device according to any of the previous embodiments, wherein the method further comprises communicating the hypoglycemic risk measure 299 to a user of the device, a health care professional or a person related to the subject.

8. The device according to any of the previous embodiments, wherein the further comprises the step of estimating a severity measure 602 of the estimated hypoglycemic risk measure 299, wherein evaluating the severity $t_{hypo}$, comprises using the relations:

$$t_{hypo} = \frac{G_{low} - G}{h_G}$$

wherein,
$G_{low}$ is a lower limit 512 of the glucose level,
G is the glucose level at the evaluation time,
$h_G$ is the evaluated rate of change of glucose 264.

9. The device according to any of the previous embodiments, wherein the binary risk expressions further comprises:
(iv) an evaluated rate of change of insulin on board at the evaluation time 261 is negative, and numerically smaller than an evaluated historical rate of change of insulin on board evaluated at the reference historical time, and wherein the evaluated historical rate of change of insulin on board evaluated at the reference historical time is also negative.

10. The device according to any of the previous embodiments, wherein the binary risk expressions further comprises:
(v) an evaluated rate of change of insulin on board at the evaluation time 261 is positive, and numerically larger than an evaluated historical rate of change of insulin on board evaluated at the reference historical time, and wherein the evaluated historical rate of change of insulin on board evaluated at the reference historical time is also positive.

11. The device according to any of the previous embodiments, wherein the binary risk expressions further comprises:
(vi) an evaluated rate of change of insulin on board at the evaluation time 261 is positive, and an evaluated historical rate of change of insulin on board evaluated at the reference historical time is negative.

12. A method for estimating the risk of a future hypoglycemic event for a subject with a standing insulin regimen 206, wherein the standing insulin regimen comprises one or more types of insulin medicament dosage regimen 208, wherein each of the one or more types of insulin medicament dosage regimen 208 comprises a type of insulin medicament 210 defining one or more types of insulin medicaments, the method comprises:
using a device 250, wherein the device comprises one or more processors 274 and a memory 192/290, the memory storing:
for each of the type of insulin medicament 210, a duration of action profile 212 predicting the insulin remaining in the subject as a function of time and characterized by a duration of the respective insulin medicament,
a historical data set 218 comprising historical insulin on board data 219 for the subject as a function of time within a historical time course, historical glucose measurements 240 of the subject and corresponding timestamps 242 obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen a plurality of historical time period records 244, wherein each of the historical time period records 245 comprises an identified historical metabolic state 246 of the subject, a respective type of metabolic state 247, and a corresponding historical time period in adherence 248, wherein the corresponding historical time period in adherence 248 is one of the plurality of historical time periods in adherence;

the memory further storing instructions that, when executed by the one or more processors 274, perform a method of:

obtaining a first data set 220 from one or more insulin injection devices used by the subject to apply the standing insulin regimen 206, the first data set 220 comprising a plurality of insulin medicament records over a time course, each respective insulin medicament record 222 in the plurality of medicament records comprising:
(i) a respective insulin medicament injection event 224 including an amount of insulin medicament 228 injected into the subject using a respective insulin injection device 104 in the one or more insulin injection devices, and
(ii) a corresponding electronic injection event timestamp 226 within the time course that is automatically generated by the respective insulin injection device 104 upon occurrence of the respective insulin medicament injection event 224,
(iii) a respective type of insulin medicament injected 230 into the subject from one or more types of insulin medicaments;

obtaining a second data set 235, the second data set comprising a plurality of autonomous glucose measurements of the subject and, for each respective autonomous glucose measurement 236 in the plurality of autonomous glucose measurements, a glucose measurement timestamp 238 representing when the respective measurement 236 was made, wherein the glucose measurements and the corresponding timestamps, are structured to allow a derivation of a first derivative with respect to time and thereby to obtain an evaluated glucose concentration and a rate of change of glucose as a function of time;

using the second data set 235 to obtain a current blood glucose event 255 associated with the subject, wherein the current blood glucose event 255 indicates the beginning of an evaluation period 260 relating to an evaluation of a current metabolic state 256 of the subject, wherein the current metabolic state 256 is having a respective type of metabolic state 257;

responsive to an identification of the current blood glucose event 255 associated with the subject at a given time, evaluating the hypoglycemic risk at an evaluation time 261 within the evaluation period by:
using the second data set 235 to obtain the type of metabolic state 257 of the current metabolic state 256;

using the first data set 220 to obtain an evaluated insulin on board of the subject 502, wherein the evaluated insulin on board is calculated from a total amount of insulin medicament injected into the subject indicated by the medicament records 222 in the first data set 220 having injection event timestamps 226 that are within the duration of the respective insulin medicament to the evaluation time, wherein the evaluation utilizes the duration of action profile of the indicating medicament records 222, using the second data set to obtain:
(i) an evaluated glucose concentration 263 at the evaluation time,
(ii) an evaluated rate of change of glucose 264 at the evaluation time;

responsive to the evaluated rate of change 264 being negative:
using the plurality of historical time period records to obtain:
(i) a reference historical metabolic state 265 of the subject, by selecting a historical time period record 245, comprising a historical metabolic state 246 having the same type of metabolic state 247 as the current metabolic state 256, wherein the selected historical time period record 245 defines a reference historical time period record,
(ii) a reference historical time period 266 corresponding to the reference historical time period record,
(iii) a reference historical time 267, by selecting a time within the reference historical time period 266, wherein a progression of the reference historical metabolic state 265 is comparable to the progression of the current metabolic state 256 at the evaluation time 261;
estimating a hypoglycemic risk measure 299 wherein the hypoglycemic risk measure (299) is an increasing function with the number of binary risk expressions being true, wherein the binary risk expressions are:
(i) the evaluated glucose concentration 263 is smaller than an evaluated historical glucose concentration 270 evaluated at the reference historical time 267,
(ii) an evaluated rate of change of glucose 264 is numerically larger than an evaluated historical rate of change of glucose 267 evaluated at the reference historical time 267,
(iii) an evaluated insulin on board 262 evaluated at the evaluation time 261 is larger than an evaluated historical insulin on board 272 evaluated at the reference historical time 267.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for estimating the risk of a future hypoglycemic event for a subject with a standing insulin regimen, wherein the standing insulin regimen comprises one or more types of insulin medicament dosage regimen, wherein each of the one or more types of insulin medicament dosage regimen comprises a type of insulin medicament defining one or more types of insulin medicaments;
wherein the device comprises a display, one or more processors, and a memory, the memory storing:
deliverable dosage data of one or more types of insulin medicament, and for each of the type of insulin medicament, a duration of action profile for predicting the insulin remaining in the subject as a function of time and characterized by a duration of the respective insulin medicament, wherein the type of insulin medicament can contribute to an insulin on board evaluation when a corresponding injection event has a time stamp within the duration from an evaluation time,
a historical data set comprising historical insulin on board data for the subject as a function of time within a historical time course, historical glucose measurements of the subject and corresponding timestamps obtained within the historical time course, wherein the historical glucose measurements and the corresponding timestamps, are structured to allow a derivation of a first derivative with respect to time and thereby to obtain an evaluated historical glucose concentration, and an evaluated historical rate of change of glucose as a function of time, and wherein the historical time course comprises a plurality of historical time periods in adherence, wherein the subject has been in adherence with the standing insulin regimen, and
a plurality of historical time period records obtained from the historical data set, wherein each of the historical time period records comprises an identified historical metabolic state of the subject, a historical blood glucose event, wherein the historical metabolic state can be identified by the historical blood glucose event, wherein the historical blood glucose event can be identified as a pattern in the historical glucose measurements of the historical data set, a respective type of metabolic state, and a corresponding historical time period in adherence with the standing insulin regimen, wherein the corresponding historical time period in adherence is one of the plurality of historical time periods in adherence;
the memory further storing instructions that, when executed by the one or more processors, cause the one or more processors to perform a method of:

obtaining a first data set from one or more insulin injection devices used by the subject to apply the standing insulin regimen, the first data set comprising a plurality of insulin medicament records over a time course following the historical time course, each respective insulin medicament record in the plurality of medicament records comprising:
(i) a respective insulin medicament injection event including an amount of insulin medicament injected into the subject using a respective insulin injection device in the one or more insulin injection devices,
(ii) a corresponding electronic injection event timestamp within the time course that is automatically generated by the respective insulin injection device upon occurrence of the respective insulin medicament injection event, and
(iii) a respective type of insulin medicament injected into the subject from one or more types of insulin medicaments;

obtaining a second data set, the second data set comprising a plurality of autonomous glucose measurements of the subject and, for each respective autonomous glucose measurement in the plurality of autonomous glucose measurements, a glucose measurement timestamp representing when the respective measurement was made, wherein the glucose measurements and the corresponding timestamps, are structured to allow a derivation of a first derivative with respect to time and thereby to obtain an evaluated glucose concentration and a rate of change of glucose as a function of time;

using the second data set to obtain a current blood glucose event associated with the subject, wherein the current blood glucose event can be identified as a pattern in the autonomous glucose measurements of the second data set, wherein the current blood glucose event identifies the beginning of an evaluation period relating to an evaluation of a current metabolic state of the subject, wherein the current metabolic state has a respective type of metabolic state;

responsive to an identification of the current blood glucose event associated with the subject at a given time, evaluating the hypoglycemic risk at an evaluation time within the evaluation period by:
using the second data set to obtain the type of metabolic state of the current metabolic state;
using the first data set to obtain an evaluated insulin on board of the subject, wherein the evaluated insulin on board is calculated from a total amount of insulin medicament injected into the subject indicated by the medicament records in the first data set having injection event timestamps that are within the duration of the respective insulin medicament to the evaluation time, and therefore contribute to the insulin on board, wherein the evaluation utilizes the duration of action profile of the medicament records indicating the total amount of insulin medicament injected,
using the second data set to obtain:
(i) an evaluated glucose concentration at the evaluation time, and
(ii) an evaluated rate of change of glucose at the evaluation time; and responsive to the evaluated rate of change being negative:
using the plurality of historical time period records to obtain:
(i) a reference historical metabolic state of the subject, by selecting a historical time period record, comprising a historical metabolic state having the same type of metabolic state as the current metabolic state, wherein the selected historical time period record defines a reference historical time period record,
(ii) a reference historical time period corresponding to the reference historical time period record, and
(iii) a reference historical time, by selecting a time within the reference historical time period, wherein a progression of the reference historical metabolic state at the reference historical time is comparable to the progression of the current metabolic state at the evaluation time;
estimating a hypoglycemic risk measure wherein the hypoglycemic risk measure is an increasing function with the number of binary risk expressions being true, wherein the binary risk expressions are:
(i) the evaluated glucose concentration is smaller than an evaluated historical glucose concentration evaluated at the reference historical time,
(ii) an evaluated rate of change of glucose is numerically larger than an evaluated historical rate of change of glucose evaluated at the reference historical time, and
(iii) an evaluated insulin on board evaluated at the evaluation time is larger than an evaluated historical insulin on board evaluated at the reference historical time, and
communicating to the subject, via the display, an estimate of the risk of a future hypoglycemic event.

2. The device according to claim 1, wherein the step of using the second data set to identify a current blood glucose event associated with the subject comprises:
responsive to receiving an indication of a meal, using the second data set to identify a maximum glucose concentration as the glucose pattern indicating the current blood glucose event, and
identifying a time of maximum glucose concentration, corresponding to the identified maximum glucose concentration, and thereby identifying the beginning of the evaluation period, and wherein the current metabolic state is a postprandial state.

3. The device according to claim 1, wherein the step of using the second data set to identify a current blood glucose event associated with the subject comprises:
evaluating a moving period of variance $\sigma^2$,
in response to the moving period of variance satisfying a predefined selection criteria, selecting the evaluated moving period of variance as an indication of the beginning of the evaluation period, wherein the selected evaluated moving period of variance defines a selected moving period of variance.

4. The device according to claim 3, the memory further storing instructions that, when executed by the one or more processors, cause the one or more processors to perform the step of:
identifying the beginning of the evaluation period, as the time for the beginning of the selected moving period of variance, and wherein the current metabolic state is a current fasting period.

5. The device according to claim 3, wherein
evaluating the moving period of variance $\sigma_k^2$ across the plurality of autonomous glucose measurements comprises using the relations:

$$\sigma_k^2 = \frac{1}{M} \sum_{i=k-M+1}^{k} (G_i - \overline{G})^2$$

wherein,
- $G_i$ is the $i^{th}$ autonomous glucose measurement in a portion k of the plurality of autonomous glucose measurements,
- M is a number of autonomous glucose measurements in the plurality of glucose measurements and represents a contiguous predetermined time span,
- $\overline{G}$ is the mean of the autonomous glucose measurements selected from the plurality of autonomous glucose measurements, and
- k is within the first time period; and wherein the predefined selection criteria is: the moving period of variance $\sigma_k^2$ is smaller than a predetermined threshold.

6. The device according to claim 1, wherein the insulin medicament dosage regimen comprises a bolus insulin medicament dosage regimen with a short acting insulin medicament, and a basal insulin medicament dosage regimen with a long acting insulin medicament; wherein
the duration of action profile for the one or more types of insulin medicament comprises:
a bolus duration of action profile for the short acting insulin medicament that is characterized by a duration of the short acting insulin medicament, and
a basal duration of action profile for the long acting insulin medicament that is characterized by a duration of the long acting insulin medicament; wherein
using the first data set to calculate an evaluated insulin on board of the subject comprises adding an insulin on board relating to the short acting insulin medicament with an insulin on board relating to the long acting insulin medicament, wherein
the insulin on board relating to the short acting insulin medicament is calculated from a total amount of short acting insulin medicament injected into the subject indicated by the medicament records in the first data set having injection event timestamps that are within the duration of the short acting insulin medicament to the evaluation time, and wherein
the insulin on board relating to the long acting insulin medicament is calculated from a total amount of long acting insulin medicament injected into the subject indicated by the medicament records in the first data set having injection event timestamps that are within the duration of the long acting insulin medicament to the evaluation time.

7. The device according to claim 1, the memory further storing instructions that, when executed by the one or more processors, cause the one or more processors to perform the step of communicating the hypoglycemic risk measure to a user of the device, a health care professional or a person related to the subject.

8. The device according to claim 1, the memory further storing instructions that, when executed by the one or more processors, cause the one or more processors to perform the step of estimating a severity measure of the estimated hypoglycemic risk measure, wherein evaluating the severity measure ($t_{hypo}$), comprises using the relations:

$$t_{hypo} = \frac{G_{low} - G}{h_G}$$

wherein,
- $G_{low}$ is a lower limit of the glucose level,
- G is the glucose level at the evaluation time, and
- $h_G$ is the evaluated rate of change of glucose.

9. The device according to claim 1, wherein the binary risk expressions further comprise:
(iv) an evaluated rate of change of insulin on board at the evaluation time is negative, and numerically smaller than an evaluated historical rate of change of insulin on board evaluated at the reference historical time, and wherein the evaluated historical rate of change of insulin on board evaluated at the reference historical time is also negative.

10. The device according to claim 9, wherein the binary risk expressions further comprise:
(v) an evaluated rate of change of insulin on board at the evaluation time is positive, and numerically larger than an evaluated historical rate of change of insulin on board evaluated at the reference historical time, and wherein the evaluated historical rate of change of insulin on board evaluated at the reference historical time is also positive.

11. The device according to claim 10, wherein the binary risk expressions further comprise:
(vi) an evaluated rate of change of insulin on board at the evaluation time is positive, and an evaluated historical rate of change of insulin on board evaluated at the reference historical time is negative.

12. The device according to claim 1, wherein for the historical blood glucose event of the plurality of historical time period records, the subject did not experience a hypoglycemic event in a period following the blood glucose event.

* * * * *